(12) United States Patent
Wiseman et al.

(10) Patent No.: US 11,426,402 B2
(45) Date of Patent: Aug. 30, 2022

(54) IRE1 ACTIVATING COMPOUNDS FOR USE IN THERAPY

(71) Applicant: The Scripps Research Institute, La Jolla, CA (US)

(72) Inventors: R. Luke Wiseman, Chula Vista, CA (US); Jeffery W. Kelly, La Jolla, CA (US); Julia M. D. Grandjean, San Diego, CA (US); Christina B. Cooley, San Antonio, TX (US); Lars Plate, Nashville, TN (US); Enrique Saez, San Diego, CA (US); Aparajita Madhavan, San Diego, CA (US); Bernard Kok, La Jolla, CA (US)

(73) Assignee: The Scripps Research Institute, La Jolla, GA (US)

( * ) Notice: Subject to any disclaimer, the term of this patent is extended or adjusted under 35 U.S.C. 154(b) by 0 days.

(21) Appl. No.: 15/929,849

(22) Filed: May 26, 2020

(65) Prior Publication Data
US 2021/0008064 A1 Jan. 14, 2021

Related U.S. Application Data

(60) Provisional application No. 63/023,523, filed on May 12, 2020, provisional application No. 62/704,237, filed on Apr. 29, 2020, provisional application No. 62/872,114, filed on Jul. 9, 2019.

(51) Int. Cl.
| | |
|---|---|
| *A61K 31/497* | (2006.01) |
| *A61K 31/404* | (2006.01) |
| *A61K 31/415* | (2006.01) |
| *A61K 31/4439* | (2006.01) |
| *A61K 31/454* | (2006.01) |
| *A61K 31/517* | (2006.01) |
| *A61K 31/522* | (2006.01) |
| *A61K 31/519* | (2006.01) |
| *A61P 9/10* | (2006.01) |
| *A61P 25/28* | (2006.01) |
| *A61P 3/10* | (2006.01) |
| *A61P 25/16* | (2006.01) |

(52) U.S. Cl.
CPC .......... *A61K 31/497* (2013.01); *A61K 31/404* (2013.01); *A61K 31/415* (2013.01); *A61K 31/4439* (2013.01); *A61K 31/454* (2013.01); *A61K 31/517* (2013.01); *A61K 31/522* (2013.01)

(58) Field of Classification Search
CPC .. A61K 31/497; A61K 31/454; A61K 31/517; A61K 31/404; A61K 31/522; A61K 31/4439; A61K 31/415; A61K 31/519; A61P 9/10; A61P 25/28; A61P 3/10; A61P 25/16
See application file for complete search history.

(56) References Cited

U.S. PATENT DOCUMENTS

2012/0264744 A1   10/2012   Dasgupta et al.

FOREIGN PATENT DOCUMENTS

| WO | 2005108599 | 11/2005 | |
| WO | WO-2009097113 A2 * | 8/2009 | ......... A61K 31/4025 |
| WO | 2021007594 | 1/2021 | |

OTHER PUBLICATIONS

Paula, P-C., "Preventive effect of quercetin in a triple transgenic Alzheimer's disease mice model." Molecules 24.12 (2019): 2287.*
Bureau, G., "Resveratrol and quercetin, two natural polyphenols, reduce apoptotic neuronal cell death induced by neuroinflammation." Journal of neuroscience research 86.2 (2008): 403-410.*
Gibrat, C., "Differences between subacute and chronic MPTP mice models: investigation of dopaminergic neuronal degeneration and α-synuclein inclusions." Journal of neurochemistry 109.5 (2009): 1469-1482.*
Horowitz, M.,"New directions in Gaucher disease." Human mutation 37.11 (2016): 1121-1136.*
U.S. Appl. No. 62/872,114, Express Abandonment with Addendum filed May 6, 2020, 5 pgs.
U.S. Appl. No. 62/872,114, Response to Request by a Person Not Authorized to Submit Request dated May 8, 2020, 1 pg.
U.S. Appl. No. 62/872,114, Powerof Attorney and Statement Under 3.73 filed May 8, 2020, 6 pgs.
U.S. Appl. No. 62/872,114, Express Abandonment and Addendum filed May 11, 2020, 5 pgs.
U.S. Appl. No. 62/872,114, Notice Regarding PowerofAttorney dated May 13, 2020, 1 pg.
U.S. Appl. No. 62/872,114, Response to Request by a Person Not Authorized to Submit Request dated May 13, 2020, 1 pg.
U.S. Appl. No. 62/872,114, Response to Request for Corrected Filing Receipt dated May 13, 2020, 1 pg.
U.S. Appl. No. 62/704,237, Express Abandonment with Addendum filed May 11, 2020, 14 pgs.
U.S. Appl. No. 62/704,237, Notice of Abandonment dated May 21, 2020, 1 pg.
"International Application Serial No. PCT US2020 070251, International Search Report dated Nov. 3, 2020", 5 pgs.
"International Application Serial No. PCT US2020 070251, Written Opinion dated Nov. 3, 2020", 6 pgs.

(Continued)

*Primary Examiner* — John M Mauro
(74) *Attorney, Agent, or Firm* — Rimon, P.C.; Dale L. Rieger

(57) ABSTRACT

Disclosed herein are compounds, their pharmaceutical salts, and pharmaceutical compositions that selectively activate the inositol-requiring enzyme 1 (IRE1)/X-box binding protein 1 (XBP1s) signaling pathway of the unfolded protein response (UPR), but that do not target the IRE1 kinase domain. The compounds are useful in treating diseases or conditions characterized by imbalances in proteostasis within the endoplasmic reticulum (ER) or secretory pathway, including those not associated with ER stress or activation of UPR.

22 Claims, 14 Drawing Sheets

(56) References Cited

OTHER PUBLICATIONS

Dooley, Christina B, "Unfolded protein response activation reduces secretion and extracellular aggregation of amyloidogenic immunoglobulin light chain", PNAS, vol. 111, No. 36, (Sep. 9, 2014), 13046-13051.
Jiang, Dadi, "Targeting the IRE1 [alpha]-XBP1 branch of the unfolded protein response in human", Seminars in Cancer Biology, vol. 33, (2015), 48-56.
Plate, Lars, "Small molecule proteostasis regulators that reprogram the ER to reduce extracellular protein aggregation", ELIFE, vol. 5, (Jul. 20, 2016), 49 pgs.
Chakrabarti, A.; Chen, A. W.; Varner, J. D., A review of the mammalian unfolded protein response. Biotechnol Bioeng 2011, 108(12), 2777-93.
Walter, P.; Ron, D., The unfolded protein response: from stress pathway to homeostatic regulation. Science 2011, 334 (6059), 1081-6.
Bernales, S.; Papa, F. R.; Walter, P., Intracellular signaling by the unfolded protein response. Annu Rev Cell Dev Biol 2006, 22, 487-508.
Schroder, M.; Kaufman, R. J., ER stress and the unfolded protein response. Mutat Res 2005, 569 (1-2), 29-63.
Zhang, K.; Kaufman, R. J., Signaling the unfolded protein response from the endoplasmic reticulum. J Biol Chem 2004, 279 (25), 25935-8.
Patil, C.; Walter, P., Intracellular signaling from the endoplasmic reticulum to the nucleus: the unfolded protein response in yeast and mammals. Curr Opin Cell Biol 2001, 13 (3), 349-55.
Ron, D., Translational control in the endoplasmic reticulum stress response. J Clin Invest 2002,110 (10), 1383-8.
Shoulders, M. D.; Ryno, L. M.; Genereux, J. C.; Moresco, J. J.; Tu, P. G.; Wu, C.; Yates, J. R., 3rd; Su, A. I; Kelly, J. W.; Wiseman, R. L., Stress-independent activation of XBP1s and/or ATF6 reveals three functionally diverse ER proteostasis environments. Cell Rep 2013, 3 (4), 1279-92.
Lebeau, J.; Saunders, J. M.; Moraes, V. W. R.; Madhavan, A.; Madrazo, N.; Anthony, M. C.; Wiseman, R. L., The PERK Arm of the Unfolded Protein Response Regulates Mitochondrial Morphology during Acute Endoplasmic Reticulum Stress. Cell Rep 2018, 22 (11), 2827-2836.
Lee, A. H.; Iwakoshi, N. N.; Glimcher, L. H., XBP-1 regulates a subset of endoplasmic reticulum resident chaperone genes in the unfolded protein response. Mol Cell Biol 2003, 23 (21), 7448-59.
Han, J.; Back, S. H.; Hur, J.; Lin, Y. H.; Gildersleeve, R.; Shan, J.; Yuan, C. L.; Krakowski, D.; Wang, S. Hatzoglou, M.; Kilberg, M. S.; Sartor, M. A.; Kaufman, R. J., ER-stress-induced transcriptional regulation increases protein synthesis leading to cell death. Nat Cell Biol 2013, 15 (5), 481-90.
Chang, T. K.; Lawrence, D. A.; Lu, M.; Tan, J.; Harness, J. M.; Marsters, S. A.; Liu, P.; Sandoval, W.; Martin, S. E.; Ashkenazi, A., Coordination between Two Branches of the Unfolded Protein Response Determines Apoptotic Cell Fate. Mol Cell 2018, 71 (4), 629-636 e5.
Balch, W. E.; Morimoto, R. I.; Dillin, A.; Kelly, J. W., Adapting proteostasis for disease intervention. Science 2008, 319 (5865), 916-9.
Chen, J. J.; Genereux, J. C.; Wiseman, R. L., Endoplasmic reticulum quality control and systemic amyloid disease: impacting protein stability from the inside out. IUBMB Life 2015, 67 (6), 404-13.
Wong, M. Y.; Shoulders, M. D., Targeting defective proteostasis in the collagenopathies. Curr Opin Chem Biol 2019, 50, 80-88.
Zhang, L.; Zhang, C.; Wang, A., Divergence and Conservation of the Major UPR Branch IRE1-bZIP Signaling Pathway across Eukaryotes Sci Rep 2016, 6, 27362.
Joshi, A.; Newbatt, Y.; McAndrew, P. C.; Stubbs, M.; Burke, R.; Richards, M. W.; Bhatia, C.; Caldwell, J. J. McHardy, T.; Collins, I.; Bayliss, R., Molecular mechanisms of human IRE1 activation through dimerization and ligand binding. Oncotarget 2015, 6 (15), 13019-35.
Korennykh, A. V.; Egea, P. F.; Korostelev, A. A.; Finer-Moore, J.; Zhang, C.; Shokat, K. M.; Stroud, R. M.; Walter, P., The unfolded protein response signals through high-order assembly of Ire1 Nature 2009, 457 (7230), 687-93.
Ali, M. M.; Bagratuni, T.; Davenport, E. L.; Nowak, P. R.; Silva-Santisteban, M. C.; Hardcastle, A.; McAndrews, C. Rowlands, M. G.; Morgan, G. J.; Aherne, W.; Collins, I.; Davies, F. E.; Pearl, L. H., Structure of the Ire1 autophosphorylation complex and implications for the unfolded protein response. EMBO J 2011, 30 (5), 894-905.
Wang, L.; Perera, B. G.; Hari, S. B.; Bhhatarai, B.; Backes, B. J.; Seeliger, M. A.; Schurer, S. C.; Oakes, S. A. Papa, F. R.; Maly, D. J., Divergent allosteric control of the IRE1alpha endoribonuclease using kinase inhibitors. Nat Chem Biol 2012, 8 (12), 982-9.
Yoshida, H.; Matsui, T.; Yamamoto, A.; Okada, T.; Mori, K., XBP1 mRNA is induced by ATF6 and spliced by IRE1 in response to ER stress to produce a highly active transcription factor. Cell 2001, 107 (7), 881-91.
Hollien, J.; Lin, J. H.; Li, H.; Stevens, N.; Walter, P.; Weissman, J. S., Regulated Ire1-dependent decay of messenger RNAs in mammalian cells. J Cell Biol 2009, 186 (3), 323-31.
Tufanli, O.; Telkoparan Akillilar, P.; Acosta-Alvear, D.; Kocaturk, B.; Onat, U. I.; Hamid, S. M.; Cimen, I.; Walter, P.; Weber, C.; Erbay, E., Targeting IRE1 with small molecules counteracts progression of atherosclerosis. Proc Natl Acad Sci U S A 2017, 114 (8), E1395-E1404.
Rosen, D. A.; Seki, S. M.; Fernandez-Castaneda, A.; Beiter, R. M.; Eccles, J. D.; Woodfolk, J. A.; Gaultier, A., Modulation of the sigma-1 receptor-IRE1 pathway is beneficial in preclinical models of inflammation and sepsis. Sci Transl Med 2019, 11 (478).
Wang, S.; Kaufman, R. J., The impact of the unfolded protein response on human disease. J Cell Biol 2012, 197 (7), 857-67.
Zhou, Y. et al. Regulation of glucose homeostasis through a XBP-1-FoxO1 interaction. Nat Med 17, 356-365, doi:10.1038/nm.2293 (2011).
Hassler et al. The IRE1α/XBP1s Pathway Is Essential for the Glucose Response and Protection of β Cells. PLOS Biology 13, doi:10.1371/journal.pbio.1002277 (2015).
Cisse, M., et al.. The transcription factor XBP1s restores hippocampal synaptic plasticity and memory by control of the Kalirin-7 pathway in Alzheimer model. Mol Psychiatry, 2017. 22(11): p. 1562-1575.
Gerakis, Y., et al., Abeta42 oligomers modulate beta-secretase through an XBP-1s-dependent pathway involving HRD1. Sci Rep, 2016. 6: p. 37436.
Martinez, G., et al., Regulation of Memory Formation by the Transcription Factor XBP1. Cell Rep, 2016. 14(6): p. 1382-1394.
Loewen, C.A. and M.B. Feany, The unfolded protein response protects from tau neurotoxicity in vivo. PLoS One, 2010. 5(9).
Sado, M., et al., Protective effect against Parkinson's disease-related insults through the activation of XBP1. Brain Res, 2009. 1257: p. 16-24).
Ryoo, H.D., et al., Unfolded protein response in a *Drosophila* model for retinal degeneration. EMBO J, 2007. 26(1): p. 242-52).
Sheng, X., et al. (2019). IRE1α-XBP1s pathway promotes prostate cancer by activating c-MYC signaling. Nature Communications, 10(1), 323.
E. Chevet et al., Endoplasmic Reticulum Stress-Activated Cell Reprogramming in Oncogenesis, Cancer Discov. 2015(5) (6) 586-597.
Tam, A. B.; Koong, A. C.; Niwa, M., Ire1 has distinct catalytic mechanisms for XBP1/HAC1 splicing and RIDD. Cell Rep 2014,9 (3), 850-8.
Bae, D.; Moore, K. A.; Melia, J. M.; Hayashi, S. Y.; Hollien, J., Degradation of Blos1 mRNA by IRE1 repositions lysosomes and protects cells from stress. J Cell Biol 2019, 218 (4), 1118-1127.
Lin, J. H.; Li, H.; Yasumura, D.; Cohen, H. R.; Zhang, C.; Panning, B.; Shokat, K. M.; Lavail, M. M.; Walter, P., IRE1 signaling affects cell fate during the unfolded protein response. Science 2007, 318 (5852), 944-9.
Valdes, P.; Mercado, G.; Vidal, R. L.; Molina, C.; Parsons, G.; Court, F. A.; Martinez, A.; Galleguillos, D.; Armentano, D.; Schneider, B. L.; Hetz, C., Control of dopaminergic neuron survival by the

(56) References Cited

OTHER PUBLICATIONS unfolded protein response transcription factor XBP1. Proc Natl Acad Sci U S A 2014, 111 (18), 6804-9.
Zuleta, A.; Vidal, R. L.; Armentano, D.; Parsons, G.; Hetz, C., AAV-mediated delivery of the transcription factor XBP1s into the striatum reduces mutant Huntingtin aggregation in a mouse model of Huntington's disease. Biochem Biophys Res Commun 2012, 420 (3), 558-63.
Valenzuela, V.; Collyer, E.; Armentano, D.; Parsons, G. B.; Court, F. A.; Hetz, C., Activation of the unfolded protein response enhances motor recovery after spinal cord injury. Cell Death Dis 2012, 3, e272.
Chiang, W. C.; Messah, C.; Lin, J. H., IRE1 directs proteasomal and lysosomal degradation of misfolded rhodopsin. Mol Biol Cell 2012, 23 (5), 758-70.
Sifers, R. N., Intracellular processing of alpha1-antitrypsin. Proc Am Thorac Soc 2010, 7 (6), 376-80.
Cui, H.; Deng, M.; Zhang, Y.; Yin, F.; Liu, J., Geniposide Increases Unfolded Protein Response-Mediating HRD1 Expression to Accelerate APP Degradation in Primary Cortical Neurons. Neurochem Res 2018, 43 (3), 669-680.
Kaneko, M.; Koike, H.; Saito, R.; Kitamura, Y.; Okuma, Y; Nomura, Y., Loss of HRD1-mediated protein degradation causes amyloid precursor protein accumulation and amyloid-beta generation. J Neurosci 2010, 30 (11), 3924-32.
Ozcan, U.; Cao, Q.; Yilmaz, E.; Lee, A. H.; Iwakoshi, N. N.; Ozdelen, E.; Tuncman, G.; Gorgun, C.; Glimcher, L. H.; Hotamisligil, G. S., Endoplasmic reticulum stress links obesity, insulin action, and type 2 diabetes. Science 2004, 306 (5695), 457-61.
Bi, X.; Zhang, G.; Wang, X.; Nguyen, C.; May, H. I.; Li, X.; Al-Hashimi, A. A.; Austin, R. C.; Gillette, T. G.; Fu, G.; Wang, Z. V.; Hill, J. A., Endoplasmic Reticulum Chaperone GRP78 Protects Heart From Ischemia/Reperfusion Injury Through Akt Activation. Circ Res 2018, 122 (11), 1545-1554.
Mendez, A. S.; Alfaro, J.; Morales-Soto, M. A.; Dar, A. C.; McCullagh, E.; Gotthardt, K.; Li, H.; Acosta-Alvear, D. Sidrauski, C.; Korennykh, A. V.; Bernales, S.; Shokat, K. M.; Walter, P., Endoplasmic reticulum stress-independent activation of unfolded protein response kinases by a small molecule ATP-mimic. Elife 2015, 4.
Ghosh, R.; Wang, L.; Wang, E. S.; Perera, B. G.; Igbaria, A.; Morita, S.; Prado, K.; Thamsen, M.; Caswell, D.; Macias, H.; Weiberth, K. F.; Gliedt, M. J.; Alavi, M. V.; Hari, S. B.; Mitra, A. K.; Bhhatarai, B.; Schurer, S. C.; Snapp, E. L.; Gould, D. B.; German, M. S.; Backes, B. J.; Maly, D. J.; Oakes, S. A.; Papa, F. R., Allosteric inhibition of the IRE1 alpha RNase preserves cell viability and function during endoplasmic reticulum stress. Cell 2014, 158 (3), 534-48.
Calamini, B.; Silva, M. C.; Madoux, F.; Hutt, D. M.; Khanna, S.; Chalfant, M. A.; Saldanha, S. A.; Hodder, P.; Tait, B. D.; Garza, D.; Balch, W. E.; Morimoto, R. I., Small-molecule proteostasis regulators for protein conformational diseases. Nat Chem Biol 2011, 8 (2), 185-96.
Merour, J. Y.; Buron, F.; Ple, K.; Bonnet, P.; Routier, S., The azaindole framework in the design of kinase inhibitors. Molecules 2014, 19(12), 19935-79.
Lu, P. D.; Jousse, C.; Marciniak, S. J.; Zhang, Y.; Novoa, L; Scheuner, D.; Kaufman, R. J.; Ron, D.; Harding, H. P., Cytoprotection by pre-emptive conditional phosphorylation of translation initiation factor 2. EMBO J 2004, 23 (1), 169-79.
Xue, Z.; He, Y.; Ye, K.; Gu, Z.; Mao, Y.; Qi, L., A conserved structural determinant located at the interdomain region of mammalian inositol-requiring enzyme 1alpha. J Biol Chem 2011, 286 (35), 30859-66.
Grandjean, J. M. D.; Plate, L.; Morimoto, R. I.; Bollong, M. J.; Powers, E. T.; Wiseman, R. L., Deconvoluting Stress-Responsive Proteostasis Signaling Pathways for Pharmacologic Activation Using Targeted RNA Sequencing. ACS Chem Biol 2019, 14 (4), 784-795.
Moore, K.; Hollien, J., Ire1-mediated decay in mammalian cells relies on mRNA sequence, structure, and translational status. Mol Biol Cell 2015, 26 (16), 2873-84.
Dhow, V. W.; Mattson, M. P.; Wong, P. C.; Gleichmann, M., An overview of APP processing enzymes and products. Neuromolecular Med 2010, 12 (1), 1-12.
Portelius, E.; Olsson, M.; Brinkmalm, G.; Ruetschi, U.; Mattsson, N.; Andreasson, U.; Gobom, J.; Brinkmalm, A. Holtta, M.; Blennow, K.; Zetterberg, H., Mass spectrometric characterization of amyloid-beta species in the 7PA2 cell model of Alzheimer's disease. J Alzheimers Dis 2013, 33 (1), 85-93.
Pera, M.; Larrea, D.; Guardia-Laguarta, C.; Montesinos, J.; Velasco, K. R.; Agrawal, R. R.; Xu, Y.; Chan, R. B.; Di Paolo, G.; Mehler, M. F.; Perumal, G. S.; Macaluso, F. P.; Freyberg, Z. Z.; Acin-Perez, R.; Enriquez, J. A.; Schon, E. A.; Area-Gomez, E., Increased localization of APP-C99 in mitochondria-associated ER membranes causes mitochondrial dysfunction in Alzheimer disease. EMBO J 2017, 36 (22), 3356-3371.
Krako, N.; Magnifico, M. C.; Arese, M.; Meli, G.; Forte, E.; Lecci, A.; Manca, A.; Giuffre, A.; Mastronicola, D.; Sarti, P.; Cattaneo, A., Characterization of mitochondrial dysfunction in the 7PA2 cell model of Alzheimer's disease. J Alzheimers Dis 2013, 37 (4), 747-58.
Rainbolt, T. K.; Lebeau, J.; Puchades, C.; Wiseman, R. L., Reciprocal Degradation of YME1L and OMA1 Adapts Mitochondrial Proteolytic Activity during Stress. Cell Rep 2016, 14 (9), 2041-2049.
Blackwood, E. A.; Azizi, K.; Thuerauf, D. J.; Paxman, R. J.; Plate, L.; Kelly, J. W.; Wiseman, R. L.; Glembotski, C. C., Pharmacologic ATF6 activation confers global protection in widespread disease models by reprograming cellular proteostasis. Nat Commun 2019, 10 (1), 187.
Kroeger, H.; Grimsey, N.; Paxman, R.; Chiang, W. C.; Plate, L.; Jones, Y.; Shaw, P. X.; Trejo, J.; Tsang, S. H.; Powers, E.; Kelly, J. W.; Wiseman, R. L.; Lin, J. H., The unfolded protein response regulator ATF6 promotes mesodermal differentiation. Sci Signal 2018, 11 (517).
Casas-Tinto, S.; Zhang, Y.; Sanchez-Garcia, J.; Gomez-Velazquez, M.; Rincon-Limas, D. E.; Fernandez-Funez, P., The ER stress factor XBP1s prevents amyloid-beta neurotoxicity. Hum Mol Genet 2011, 20 (11), 2144-60.
Oslowski, et al. Methods Enzymol. 2011, 490, 71-92.
Maor, et al. Orphanet J. Rare Dis. 2013, 8, 140.
Farfel-Becker, et al. Human Mol. Gen. 2009, 18(8), 1482-1488.

\* cited by examiner

IRE1 ACTIVATING COMPOUNDS FOR USE IN THERAPY

The present application claims the benefit of priority to U.S. Provisional Applications No. 62/872,114 filed on Jul. 9, 2019, No. 62/704,237 filed on Apr. 29, 2020, and No. 63/023,523 filed on May 12, 2020, which applications are incorporated as if fully set forth herein.

STATEMENT OF GOVERNMENT SUPPORT

This invention was made with government support under grant No. AG046495 awarded by the National Institutes of Health. The U.S. government has certain rights in the invention.

BACKGROUND

The unfolded protein response (UPR) is the primary signaling pathway activated in response to endoplasmic reticulum (ER) stress[1-3]. The UPR is comprised of three signaling cascades activated downstream of the ER stress-sensing proteins IRE1, PERK, and ATF6[4-6]. In response to acute ER stress, activation of these pathways results in transcriptional and translational remodeling to alleviate the misfolded protein load in the ER lumen and promote adaptive remodeling of ER function and global cellular physiology[7-10]. However, in response to chronic or severe ER insults, prolonged UPR signaling can induce a pro-apoptotic response that results in cellular death[11,12]. Thus, through this combination of adaptive and pro-apoptotic signaling, the UPR functions at a critical intersection in dictating cellular function and survival in response to diverse pathologic insults that induce ER stress.

The capacity for UPR signaling to promote adaptive remodeling of ER function makes the three UPR signaling pathways attractive targets to ameliorate pathologic imbalances in ER proteostasis implicated in etiologically diverse diseases[13-15]. The IRE1 pathway is the most evolutionarily conserved arm of the unfolded protein response (UPR) because it is found in all organisms ranging from yeast to mammals[16]. IRE1 is an endoplasmic reticulum (ER) transmembrane protein that is activated in response to ER stress through a mechanism involving autophosphorylation and oligomerization[17-20]. This response leads to the activation of the cytosolic endoribonuclease (RNase) domain of IRE1 that is involved in the non-canonical splicing of the X-box binding protein 1 (XBP1) mRNA[21]. IRE1-dependent XBP1splicing produces an mRNA frameshift that leads to the translation of the active spliced XBP1 (or XBP1s) bZIP transcription factor[17,21]. Upon activation, XBP1s transcriptionally regulates the expression of multiple stress-responsive genes involved in diverse biological functions including ER proteostasis maintenance and lipid homeostasis[8,10]. Apart from XBP1splicing, the activated IRE1 endoribonuclease domain can also promote the degradation of ER-localized mRNAs through a process referred to as regulated IRE 1-dependent decay (or RIDD)[22,23]. While the functional implications of this IRE1 activity remain to be fully established, recent results show that RIDD serves a protective role through the selective degradation of mRNA encoding the pro-apoptotic factors (e.g., DR5) and promotion of microautophagy through the degradation of BLOS1 mRNA[22,24]. Through these mechanisms, IRE1 promotes adaptive remodeling of cellular physiology to alleviate ER stress and enhance cellular proteostasis in response to acute ER insults.

Significant genetic and chemical genetic evidence demonstrates that increasing IRE1/XBP 1s activity offers a unique opportunity to ameliorate pathologic imbalances in ER proteostasis implicated in diverse diseases. For example, stress-independent activation of a ligand-regulated IRE1 promotes cellular survival in response to chronic chemical ER insults[25]. This suggests that IRE1 activation can mitigate ER-stress associated apoptosis implicated in many neurodegenerative diseases. Consistent with this, overexpressing the activated IRE1-regulated transcription factor XBP1s promotes neuroprotection in multiple animal models of neurodegenerative disease including Parkinson's disease, Huntington's disease, and peripheral nerve injury[26-28]. Furthermore, stress-independent, chemical genetic activation of IRE1/XBP1s signaling reduces the toxic intracellular aggregation of destabilized, aggregation-prone variants of rhodopsin and α1-anti-trypsin (A1AT) implicated in retinitis pigmentosa and A1AT deficiency, respectively[8,29,30]. Increasing XBP1s activity also promotes the degradation of destabilized amyloid precursor protein (APP) mutants, reducing extracellular populations of the APP cleavage product Aβ that are genetically and pathologically implicated in Alzheimer's disease (AD)[31,32]. IRE1/XBP1s activation is also advantageous in cellular and animal models of multiple other disorders including diabetes and myocardial infarction, further highlighting the potential for enhancing IRE1signaling to improve pathologic outcomes in multiple diseases[33,34].

Some compounds allosterically activate the IRE1 RNase through binding the IRE1 nucleotide binding pocket and inhibiting IRE1 autophosphorylation[17,18,20]. While these compounds have proven useful for defining the molecular mechanism of IRE1 activation, many of these compounds show off-pathway activity and/or pleiotropic toxicity likely associated with binding nucleotide-binding pockets within other protein kinases, including PERK[20,35,36]. This off-pathway activity limits the utility of currently available IRE1 activating compounds for pharmacologic IRE1/XBP1s activation in the context of disease treatment.

SUMMARY

The present disclosure solves this problem and others by providing, in one embodiment, a method for treating a disease or condition that is characterized by imbalances in proteostasis within the endoplasmic reticulum (ER) or secretory pathway. The method comprises administering to a subject suffering from the disease or condition a therapeutically effective amount of a compound or a pharmaceutically acceptable salt thereof that selectively activates the inositol-requiring enzyme 1 (IRE1)/X-box binding protein 1 (XBP1s) signaling pathway of the unfolded protein response (UPR), wherein the compound does not target the IRE1 kinase domain.

Another embodiment of the present disclosure is a method for treating a disease or condition that is characterized by imbalances in proteostasis within the endoplasmic reticulum (ER) or secretory pathway. In this embodiment, the disease or condition is not associated with ER stress or activation of the unfolded protein response (UPR). The method comprises administering to a subject suffering from the disease or condition a therapeutically effective amount of a compound or a pharmaceutically acceptable salt thereof that selectively activates the inositol-requiring enzyme 1 (IRE1)/X-box binding protein 1 (XBP1s) signaling pathway of the unfolded protein response (UPR), wherein the compound does not target the IRE1 kinase domain.

In still another embodiment, the present disclosure provides a method for selectively activating the inositol-requiring enzyme 1 (IRE1)/X-box binding protein 1 (XBP1s) signaling pathway of the unfolded protein response (UPR). The method comprises administering to a cell a compound or a pharmaceutically acceptable salt thereof wherein the compound does not target the IRE1 kinase domain.

BRIEF DESCRIPTION OF THE DRAWINGS

(FIG. 8C). Hepatic triglyceride content (FIG. 8D) and gene expression profiles of gluconeogenic genes (FIG. 8E) at 6 weeks post dosing.

DETAILED DESCRIPTION

Figure 1:
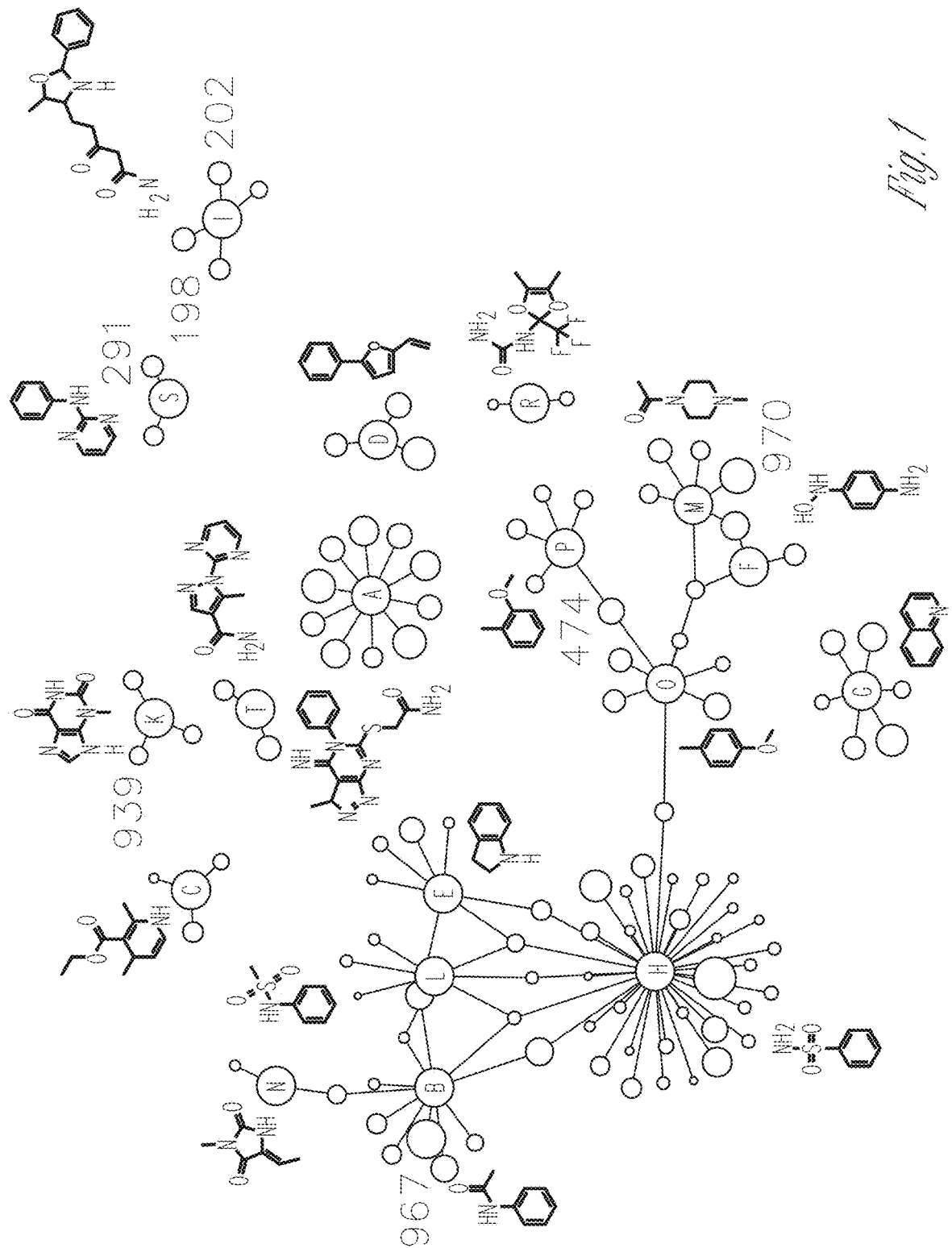
FIG. 1. Network plot illustrating shared structural motifs of a subset (99) of 128 compounds identified to preferentially activate the XBP1s-Rluc reporter to at least 20%, displayed a maximal EC50 for reporter activation of 3 µM, and a minimum toxicity IC50 of 3 µM.

The present disclosure is predicated, in part, upon the discovery of non-toxic, highly-selective compounds that activate IRE1/XBP1s signaling independent of other UPR pathways. High-throughput screening identified non-toxic compounds that selectively activate the IRE1/XBP1s arm of the UPR. The compounds activate IRE1-dependent XBP1s splicing, but do not inhibit IRE1 autophosphorylation, indicating that the compounds do not function by inhibiting the IRE1 kinase domain. Furthermore, RNAseq transcriptional profiling demonstrates that these compounds selectively activate IRE1/XBP1s signaling independent of other arms of the UPR or other stress-responsive signaling pathways.

Data described herein moreover illustrates that the compounds promote adaptive ER proteostasis remodeling through selective IRE1/XBP1s activation, which reduces the secretion of AD-relevant APP mutants and APP cleavage products through an IRE1-dependent mechanism. Further, treatment with the compounds mitigates APP-associated proteotoxicity in cell culture models. Thus, the present disclosure establishes highly-selective IRE1/XBP1s activating compounds that provide new opportunities to define mechanisms by which signaling through this pathway influences cellular physiology. These compounds can also define whether IRE1/XBP1s signaling and associated ER proteostasis remodeling is useful for ameliorating diverse pathologies in organismal models of human disease.

The development of IRE1 activating compounds has traditionally been pursued by directly targeting the IRE1 nucleotide binding pocket to induce allosteric activation of the IRE1 RNase domain. While these compounds have provided unique insights into the molecular mechanism of IRE1 activation, their utility for defining the functional implications of IRE1/XBP1s signaling is limited due to off-pathway activity, likely attributed to the binding of other kinases [20, 35, 36]. This problem defines a challenge in establishing highly-selective IRE1/XBP1s activating compounds.

The present disclosure relates in part to transcriptional selectivity for identifying compounds that activate the IRE1/XBP1s UPR signaling pathway which are suitable for probing functional implications of IRE1/XBP1s activity in cellular and organismal contexts. This approach identified compounds (e.g., 474) that selectively activate the IRE1/XBP1s UPR signaling pathway without activating other signaling arms of the UPR or other stress-responsive signaling pathways (e.g., the heat shock response or oxidative stress response). The compounds described herein moreover activate IRE1 RNase activity through a mechanism independent of binding the IRE1 nucleotide-binding pocket. This characteristic surprisingly distinguishes the compounds from currently available IRE1 activators, which directly bind the nucleotide-binding pocket to allosterically activate IRE1 RNAse activity.

Fortifying this discovery is data, described in more detail below, showing that pharmacologic IRE1 activation improves ER proteostasis of AD-relevant APP mutants, reducing the extracellular accumulation of Aβ through the increased targeting of APP to degradation. Importantly, this adaptive ER proteostasis remodeling was reversed by co-administration of the highly-selective IRE1 RNAse inhibitor 4 μ8c, confirming that the benefits afforded by the described compounds herein are attributed to IRE1-dependent signaling. The data also demonstrates that pharmacologic IRE1 activation reduces mitochondrial toxicity associated with mutant APP overexpression. This reduced mitochondrial toxicity likely reflects reduced intracellular levels of mutant APP afforded by compound treatment.

Genetic activation of IRE1/XBP1s signaling has been shown to promote protection against different types of pathologic insults associated with multiple diseases.[26-29, 34, 51]. These include, but are not limited to:

neurodegenerative diseases, such as Parkinson's Disease, Huntington's Disease, and Alzheimer's Disease (see Zuleta, A.; Vidal, R. L.; Armentano, D.; Parsons, G.; Hetz, C., AAV-mediated delivery of the transcription factor XBP1s into the striatum reduces mutant Huntington aggregation in a mouse model of Huntington's disease. *Biochem Biophys Res Commun* 2012, 420 (3), 558-63; Cui, H.; Deng, M.; Zhang, Y.; Yin, F.; Liu, J., Geniposide Increases Unfolded Protein Response-Mediating HRD1 Expression to Accelerate APP Degradation in Primary Cortical Neurons. *Neuroehem Res* 2018, 43 (3), 669-680; Casas-Tinto, S.; Zhang, Y.; Sanchez-Garcia, J.; Gomez-Velazquez, M.; Rincon-Limas, D. Fernandez-Funez. P., The ER stress factor XBP1s prevents amyloid-beta neurotoxicity. *Hum Mol Genet* 2011, 20 (11), 2144-60; Kaneko, M.; Koike, H.; Saito, R.; Kitamura, Y.; Okuma, Y.; Nomura, Y., Loss of HRD1-mediated protein degradation causes amyloid precursor protein accumulation and amyloid-beta generation. *J. Neurosci* 2010, 30 (11), 3924-32; Valdes, P.; Mercado, G.; Vidal, R. L.; Molina, C.; Parsons, G.; Court, F. A.; Martinez, A.; Galleguillos, D.; Armentano, D.; Schneider, B. L.; Hetz, C., Control of dopaminergic neuron survival by the unfolded protein response transcription factor XBP1. *Proc Natl Acad Sci USA* 2014, 111 (18). 6804-9; Cisse, M., et al., *The transcription factor XBP1s restores hippocampal synaptic plasticity and memory by control of the Kalirin-7pathway in Alzheimer model*. Mol Psychiatry, 2017. 22 (11): p. 1562-1575; Gerakis, Y., et al., Abeta42 oligomers modulate beta-secretase through an XBP-1s-dependent pathway involving HRD1. Sci Rep, 2016. 6: p. 37436; Martinez, G., et al., Regulation of Memory Formation by the Transcription Factor XBP1. Cell Rep, 2016. 14 (6): p. 1382-1394; Loewen, C. A. and M. B. Feany, The unfolded protein response protects from tau neurotoxicity in vivo. PLoS One, 2010. 5 (9); and Sado, M., et al., Protective effect against Parkinson's disease-related insults through the activation of XBP1. Brain Res, 2009. 1257: p. 16-24);

myocardial infarction (Bi, X.; Zhang, (1; Wang, X.; Nguyen, C.; May, H. Li, X.; Al-Hashimi, A. A.; Austin, R. C.; Gillette, T. G.; Fu, G.; Wang, Z. V.; Hill, J. A., Endoplasmic Reticulum Chaperone GRP78 Protects Heart From Ischemia/Reperfusion Injury Through Akt Activation. *Circ Res* 2018, 122 (11), 1545-1554);

retinitis pigmentosa (Chiang, W. C.; Messah, C.; Lin, J. H., IRE1 directs proteasomal and lysosomal degradation of misfolded rhodopsin. *Mol Biol Cell* 2012, 23 (5), 758-70); Ryoo, H. D., et al., *Unfolded protein response in a Drosophila model for retinal degeneration*. EMBO J, 2007. 26 (1): p. 242-52);

Alzheimer's Disease (Cui, H.; Deng, M.; Zhang, Y.; Yin, F.; Liu, J., Geniposide creases Unfolded Protein Response-Mediating HRD1 Expression to Accelerate APP Degradation in Primary Cortical Neurons. Neurochem Res 2018, 43 (3), 669-680; Casas-Tinto, S.; Zhang, Y.; Sanchez-Garcia, J.; Gomez-Velazquez, M.; (Rincon-Limas, D. E.; Fernandez-Funez, P., The ER stress factor XBP1s prevents amyloid-beta neurotoxicity. Hum Mol Genet 2011, 20 (11), 2144-60; Kaneko, M.; Koike, H.; Saito, R.; Kitamura, Y.; Okuma, Y.; Nomura, Y., Loss of HRD1-mediated protein degradation causes amyloid precursor protein accumulation and amyloid-beta generation. J Neurosci 2010, 30 (11), 3924-32; Cisse, M., et al., The transcription factor XBP1s restores hippocampal synaptic plasticity and memory by control of the Kalirin-7 pathway in Alzheimer model. Mol Psychiatry, 2017. 22 (11): p. 1562-1575; Gerakis, Y., et al., Abeta42 oligomers modulate beta-secretase through an XBP-1s-dependent pathway involving HRD1. Sci Rep, 2016, 6: p. 37436; Loewen, C. A. and M. B. Featly. The unfolded protein response protects from tau neurotoxicity in vivo. PLoS One, 2010. 5 (9); and Martinez, G., et al., Regulation of Memory Formation by the Transcription Factor XBP1. Cell Rep, 2016, 14(6): p. 1382-1394);

Antitrypsin Associated Emphysema (Sifers, R. N., Intracellular processing of alpha1-antitrypsin. *Proc Am ThoraC Soc* 2010. 7 (6), 376-80; and Shoulders, M. D.; Ryno, L. M.; Genereux, J. C.; Moresco, J. J.; Tu, P. G.; Wu, C.; Yates, J. R., 3rd; Su, A. I.; Kelly, J. W.; Wiseman, R. L., Stress-independent activation of XBP1s and/or ATF6 reveals three functionally diverse ER proteostasis environments. *Cell Rep* 2013, 3 (4), 1279-92);

Diabetes (Ozcan, U.; Cao, Q.; Yilmaz, E.; Lee, A. R; Iwakoshi, N. N.; Ozdelen, E.; Tuncman, G.; Gorgun, C.; Glimcher, L. H.; Hotamisligil, G. S., Endoplasmic reticulum stress links obesity, insulin action, and type 2 diabetes. *Science* 2004, 306 (5695), 457-61);

Cardiovascular Disease (Bi, X.; Zhang, G; Wang, X.; Nguyen, C.; May, H. I.; Li, X.; Al-Hashimi, A. A.; Austin, R. C.; Gillette, T. G.; Fu, G.; Wang, Z. V.; Hill, J. A., Endoplasmic Reticulum. Chaperone GRP78 Protects Heart From Ischemia/Reperfusion Injury Through Akt Activation. *Circ Res* 2018, 122 (11), 1545-1554; and Peripheral Nerve Injury (Valenzuela, V.; Collyer, E.; Armentano, D.; Parsons, G. B.; Court, F. A.; Hetz, C., Activation of the unfolded protein response enhances motor recovery after spinal cord injury. *Cell Death Dis* 2012, 3, e272).

In the context of ER stress, IRE1 activity has also been shown to promote detrimental phenotypes such as increased apoptosis and inflammation in models of diseases such as atherosclerosis and sepsis[52-54]. Furthermore, IRE1/XBP1s signaling has been shown to promote the malignant state in multiple cancers (Sheng, X., et al. (2019). IRE1α-XBP1s pathway promotes prostate cancer by activating c-MYC signaling. *Nature communications*, 10(1), 323. doi:10.1038/s41467-018-08152-3; E. Chevet et al., Endoplasmic Reticulum Stress-Activated Cell Reprogramming in Oncogenesis, *Cancer Discov.* 2015 (5) (6) 586-597). These adverse activities are potent limitations to the use of IRE1/XRP1s activating compounds in therapeutic applications.

For these reasons, pharmacologic IRE1 activation afforded by compounds such as 474 described herein offers significant advantages over genetic strategies to probe the therapeutic potential for IRE1/XBP1s activation to intervene in these diverse diseases. For example, pharmacologic IRE1 activators can selectively activate IRE1/XBP1s signaling in multiple cellular and organismal models independent of genetic manipulation. Furthermore, pharmacologic IRE1 activation allows for dosable and temporal control over IRE1/XBP1s activity through the use of different dosing regimens. Thus, the highly-selective non-toxic IRE1 activating compounds described herein (e.g., 474) can probe the functional implications of IRE1/XBP1s signaling in diverse physiologic contexts and define the therapeutic potential for activating IRE1 to mitigate pathologic imbalances in cellular or organismal physiology implicated in etiologically diverse diseases.

Definitions

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent. A therapeutically effective amount also is the minimum amount necessary to selectively activate inositol-requiring enzyme 1 (IRE1)/X-box binding protein 1 (XBP1s) signaling pathway of the unfolded protein response (UPR) while simultaneously not targeting the IRE1 kinase domain.

Generally, the initial therapeutically effective amount of a compound described herein or a pharmaceutically acceptable salt thereof that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of the compound or a pharmaceutically acceptable salt thereof. In another embodiment, such dosage forms contain from about 50 mg to about 500 mg of the compound or a pharmaceutically acceptable salt thereof. In yet another embodiment, such dosage forms contain from about 25 mg to about 200 mg of the compound or a pharmaceutically acceptable salt thereof. In still another embodiment, such dosage forms contain from about 10 mg to about 100 mg of the compound or a pharmaceutically acceptable salt thereof. In a further embodiment, such dosage forms contain from about 5 mg to about 50 mg of the compound or a pharmaceutically acceptable salt thereof. In any of the foregoing embodiments the dosage form can be administered once a day or twice per day.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

Methods and Uses

The present disclosure provides, in one embodiment, a method for treating a disease or condition that is characterized by imbalances in proteostasis within the endoplasmic reticulum (ER) or secretory pathway. The method comprises administering to a subject suffering from the disease or condition a therapeutically effective amount of a compound or a pharmaceutically acceptable salt thereof that selectively activates inositol-requiring enzyme 1 (IRE1)/X-box binding protein 1 (XBP1s) signaling pathway of the unfolded protein response (UPR), wherein the compound does not target the IRE1 kinase domain.

Another embodiment of the present disclosure is a method for treating a disease or condition that is characterized by imbalances in proteostasis within the endoplasmic reticulum (ER) or secretory pathway. In Phis embodiment, the disease or condition is not associated with ER stress or activation of the unfolded protein response (UPR). The method comprises administering to a subject suffering from the disease or condition a therapeutically effective amount of a compound or a pharmaceutically acceptable salt thereof that selectively activates inositol-requiring enzyme 1 (IRE1)/X-box binding protein 1 (XBP1s) signaling pathway of the unfolded protein response (UPR), wherein the compound does not target the IRE1 kinase domain.

In various embodiments, the disease or condition is one selected from the group consisting of diabetes, myocardial infarction, cardiovascular disease, Gaucher disease, retinal degeneration, protein misfolding disorders, and neurodegenerative diseases. Exemplary protein misfolding disorders, according to some embodiments, include amyloid diseases, Alzheimer's disease, retinal degeneration, lysosomal storage diseases, and antitrypsin associated emphysema. One particular protein misfolding disorder is Alzheimer's disease.

In other embodiments, the disease or condition is a neurodegenerative disease. Examples of neurodegenerative diseases include Parkinson's disease, Huntington's disease, and peripheral nerve injury.

In still another embodiment, the present disclosure provides a method for selectively activating the inositol-requiring enzyme 1 (IRE1)/X-box binding protein 1 (XBP1s) signaling pathway of the unfolded protein response (UPR). The method comprises administering to a cell a compound or a pharmaceutically acceptable salt thereof wherein the compound does not target the IRE1 kinase domain. The administration to the cell can occur in vivo, ex vivo, or in vitro.

In additional embodiments, optionally in combination with any other embodiment, the compound does not substantially activate stress responsive signaling pathways other than IRE 1/XBP1s.

Specific examples of the compound include those in the table below and pharmaceutically acceptable salts thereof:

198 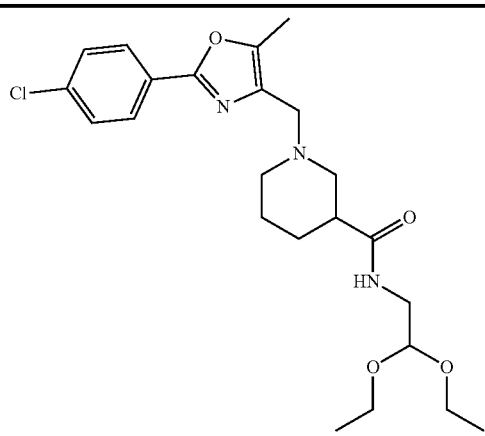

202 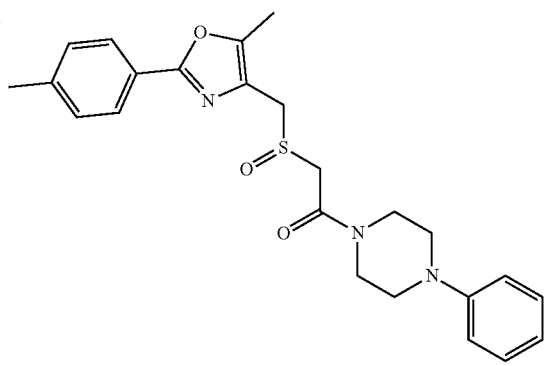 [SMILES: Cc1ccc(-c2nc(CS(=O)CC(=O)N3CCN(c4ccccc4)CC3)c(C)o2)cc1]

291 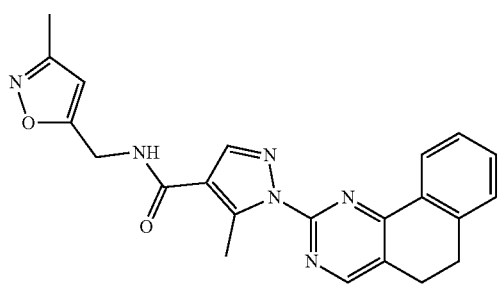 [SMILES: Cc1cc(CNC(=O)c2cnn(-c3ncc4c(n3)-c3ccccc3CC4)c2C)on1]

474 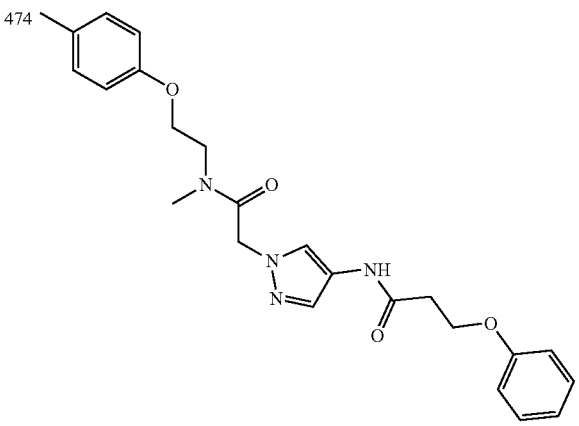

939 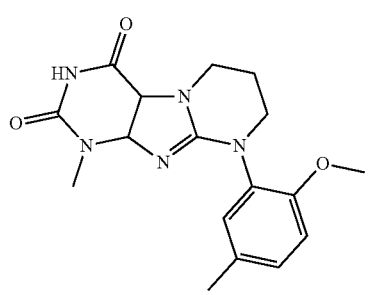 [SMILES: COc1ccc(C)cc1N1CCCN2C1=NC1C2C(=O)NC(=O)N1C]

970 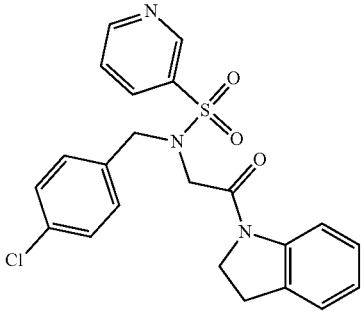 [SMILES: O=C(CN(Cc1ccc(Cl)cc1)S(=O)(=O)c1cccnc1)N1CCc2ccccc21]

967 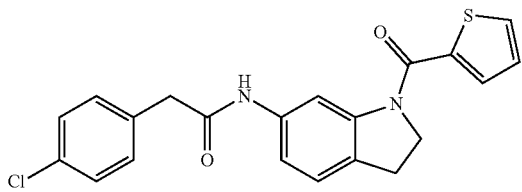 [SMILES: O=C(Cc1ccc(Cl)cc1)Nc1ccc2c(c1)N(C(=O)c1cccs1)CC2]

In some embodiments, the compound or a pharmaceutically acceptable salt thereof is chosen from the following table:

198 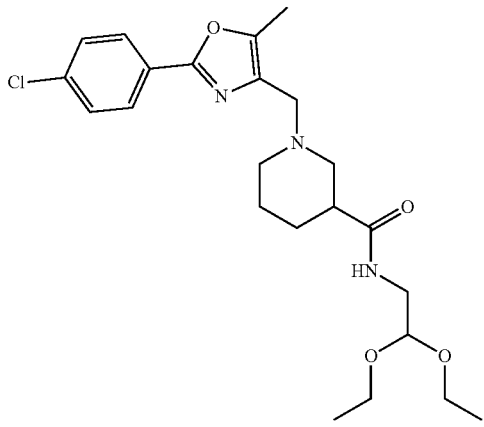 [SMILES: CCOC(CNC(=O)C1CCCN(Cc2nc(-c3ccc(Cl)cc3)oc2C)C1)OCC]

474 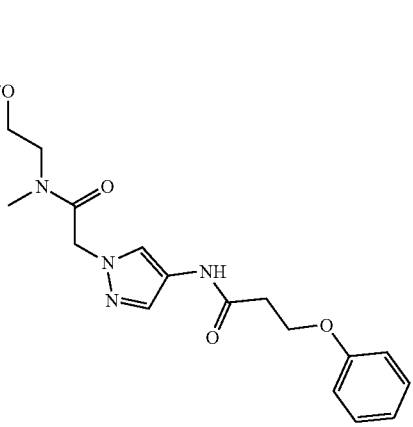

970 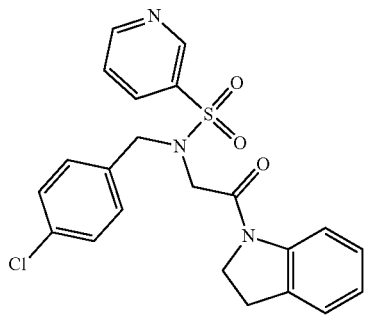 [SMILES: O=C(CN(Cc1ccc(Cl)cc1)S(=O)(=O)c1cccnc1)N1CCc2ccccc21]

The present disclosure also provides in another embodiment a pharmaceutical composition comprising a compound or pharmaceutically acceptable salt thereof as described herein in combination with a pharmaceutically acceptable carrier or excipient. Compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of the compound or a pharmaceutically acceptable salt thereof.

For tablet compositions, the compound or a pharmaceutically acceptable salt thereof in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, the compound or a pharmaceutically acceptable salt thereof is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compound or a pharmaceutically acceptable salt thereof in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the compound or a pharmaceutically acceptable salt thereof in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compound the compound or a pharmaceutically acceptable salt thereof may also be administered in the form of suppositories for rectal administration. These compositions can be prepared by mixing the compound with a suitable non-irritating excipient which is solid at ordinary temperatures but liquid at the rectal temperature and will therefore melt in the rectum to release the compound. Exemplary excipients include cocoa butter and polyethylene glycols.

Compositions for parenteral administrations are administered in a sterile medium. Depending on the vehicle used and concentration the concentration of the compound or a pharmaceutically acceptable salt thereof in the formulation, the parenteral formulation can either be a suspension or a solution containing dissolved compound. Adjuvants such as local anesthetics, preservatives and buffering agents can also be added to parenteral compositions.

EXAMPLES

Materials and Reagents

Antibodies: APP (6E10, Fisher Scientific Cat #501029533), APP (HRP-4G8, Fisher Scientific Cat 4501029498), tubulin (Sigma Cat #T6074-200UL), Sec24D (mouse) antibody was provided as a generous gift from the Balch Lab at TSRI Pharmacologics: Thapsigargin (Fisher Scientific Cat 50-464-295), 4μ8c (EMD Millipore Cat #412512), KIRA6 (Selleck Chemicals Cat #S8658)

High Throughput Screening (including all the filtering steps and the Chemical Clustering)

HEK293T-Rex cells incorporating either the XBP1s-Rluc or ERSE-FLuc reporters were collected by trypsinization and resuspended at a density of 500,000 cells per mL. The assay was started by dispensing 5 μL of cell suspension into each well of white, solid-bottom 1536-well plates using a flying reagent dispenser (FRD) and placed into an online incubator for 3 hr. Cells were then treated with 34 nL/well of either test compounds to give final concentrations of 5.17 μM, DMSO (low control, final concentration 0.68%, 0% activation) or 37 μM of Delta-7 thapsigargin (high control, final concentration 500 nM, 100% activation). Plates were incubated for 18 hr at 37° C., removed from the incubator and equilibrated to room temperature for 10 min. Luciferase activity was detected by addition of 5 μL of ONE-Glo reagent (Promega) to each well. After a 10 min incubation time, light emission was measured with the ViewLux reader (PerkinElmer).

The percent activation of each test compound was calculated as follows: % Activation=100*(Test Compound-Median Low Control)/(Median High Control Median Low Control). Primary screening of the 646,275 compound library at Scripps Florida yielded 10,114 hits for XBP1s Renilla Luciferase activity at ≥13.83% activation by thapsigargin. Compounds that hit in more than 7 screens (promiscuity score) were eliminated, as well as those that elicited HSP70 activation. The top 6,391 remaining compounds (activation≥16.36%) were moved forward to triplicate confirmation screening and HEK TREX CTG cytotoxicity counterscreening. Duplicates were removed from the resulting list, and the top 638 activating compounds (≥15.92%) were moved forward for triplicate titration screening and HEK TREX CTG titration counterscreening.

These 638 compounds were subjected to hierarchical clustering using the Library MCS application from the ChemAxon JChem Suite, grouping 551 of these by 20 conserved structural motifs, with 87 singletons. All 638 compounds were also subject to quality control measurements by LC-MS, UV-vis spectroscopy, MS, and ELSD to confirm purity and mass. Those that did not pass one of or both of these parameters were eliminated. From titration data of the remaining compounds, those with <20% reporter activation, and EC50s>3 uM were eliminated. Additionally, compounds from the HEK TREX CTG counterscreen with EC50s<3 uM were also eliminated. Remaining clustered compounds were iteratively subclustered so that the diversity of the cluster would be captured by a smaller representative group, comprised only of compounds that activated the reporter to a practical degree for in vitro measurements (>30%). Remaining singleton compounds that passed quality control and showed reporter activation>30?/o were also included for in vitro assays.

RNA-Seq Analysis (including Geneset Analysis and GO-Term Analysis)

Cells were lysed and total RNA collected using the RNeasy mini kit, according to manufacturer's instructions (Qiagen). Conventional RNA-seq was conducted via BGI Americas on the BGI Proprietary platform, providing single-end 50 bp reads at 20 million reads per sample. Alignment of sequencing data was done using DNAstar Lasergene SeqManPro to the GRCh37. p 13 human genome reference assembly, and assembly data were imported into ArrayStar 12.2 with QSeq (DNAStar Inc.) to quantify the gene expression levels and normalization to reads per kilobase per million (RPKM). Differential expression analysis and statistical significance calculations between different conditions was assessed using "DESeq" in R, compared to vehicle-treated cells, using a standard negative binomial fit of the RPKM data to generate Fold Change quantifications.

Cell Culture and Transfections

Briefly, all cells lines were cultured in high-glucose Dulbecco's Modified Eagle's Medium (DMEM; Corning-Cellgro) supplemented with 10% fetal bovine serum (FBS; Omega Scientific), 2 mM L-glutamine (Gibco), 100 U*mL$^{-1}$ penicillin, and 100 μg*mL$^{-1}$ streptomycin (Gibco). SH-SY5Y cells in galactose conditions were cultured in glucose-free Dulbecco's Modified Eagle's Medium (DMEM; Corning-Cellgro) supplemented with 10% fetal bovine serum (FBS; Omega Scientific), 2 mM L-glutamine (Gibco), 100 U*mL$^{-1}$ penicillin, and 100 μg*mL$^{-1}$ streptomycin (Gibco) and 5 mM galactose. All cells were cultured under typical tissue culture conditions (37° C., 5% $CO_2$). Cells were routinely tested for mycoplasma every 6 months. No further authentication of cell lines was performed by the authors. Cells were transfected using calcium phosphate precipitation, as previously described (3). All plasmids for transfection were prepared using the Qiagen Midiprep kit according to the manufacturers protocol. 7PA2 cells were kindly provided by Prof E, Koo (University of California, San Diego).

qPCR, Transcriptional Profiling

Primers-DNAJB9 (F: GGA AGG AGG AGC GCT AGG TC, R: ATC CTG CAC CCT CCG ACT AC), BiP (F: GCC TGT ATT TCT AGA CCT GCC, R: TTC ATC TTG CCA GCC AGT TG), CHOP (F: ACCAAGGGAGAACCAG-GAAACG, R: TCACCATTCGGTCAATCAGAGC), Ribo-Pro (F: CGT CGC CTC CTA CCT GCT, R: CCA TTC AGC TCA CTG ATA ACC TTG). The relative mRNA expression levels of target genes were measured using quantitative RT-PCR. Cells were treated as described at 37° C., washed with Dulbecco's phosphate-buffered saline (GIBCO), and then RNA was extracted using the RNeasy Mini Kit (QIAGEN). qPCR reactions were performed on cDNA prepared from 500 ng of total cellular RNA using the QuantiTect Reverse Transcription Kit (QIAGEN). The FastStart Universal SYBR Green Master Mix (Roche), cDNA, and primers purchased from Integrated DNA Technologies were used for amplifications (6 min at 95° C. then 45 cycles of 10 s at 95° C., 30 s at 60° C.) in an ABI 7900HT Fast Real Time PCR machine. Primer integrity was assessed by a thermal melt to confirm homogeneity and the absence of primer dimers. Transcripts were normalized to the housekeeping genes RiboPro and all measurements were performed in triplicate. Data were analyzed using the RQ Manager and DataAssist 2.0 softwares (ABI). qPCR data are reported as mean±95% confidence interval as calculated in DataAssist 2.0.

Immunoblotting, SDS-PAGE, and Phos-tag SDS-PAGE

Cell lysates were prepared as previously described in RIPA buffer (50 mM Tris, pH 7.5, 150 mM NaCl, 0.1% SDS, 1% Triton X-100, 0.5% deoxycholate and protease inhibitor cocktail (Roche). Total protein concentration in cellular lysates was normalized using the Bio-Rad protein assay. Lysates were then denatured with 1× Laemmli buffer+100 mM DTT and boiled before being separated by SDS-PAGE. Samples were transferred onto nitrocellulose membranes (Bio-Rad) for immunoblotting and blocked with 5% milk in Tris-buffered saline, 0.5% Tween-20 (TBST) following incubation overnight at 4° C. with primary antibodies. Membranes were washed in TBST, incubated with IR-Dye conjugated secondary antibodies and analyzed using Odyssey Infrared Imaging System (LI-COR Biosciences). Quantification was carried out with LI-COR Image Studio software.

PCR and Agarose Gel Electrophoresis

To amplify the spliced and unspliced XBP1 mRNA, XBP1 primers were used as described previously.[21] PCR products were electrophoresed on 2.5% agarose gel. GAPDH (forward 5'GGATGATGTTCTGGAGAGCC3', reverse 5'CATCACCATCTTCCAGGAGC3') was used as a loading control. The size difference between the spliced and the unspliced XBP1 is 26 nucleotides.

AB ELISA

7PA2 or 7WD10 cells were cultured on 96-well plates (Corning) and treated with IRE1 activating compounds +/−4 μ8c overnight. The medium was then replaced at 50% volume with treatment remaing, culture medium was collected after 24 hours. The medium was analyzed by an AP ELISA as follows. Monoclonal 6E10 anti-Aβ(residues 1-17) mouse IgG1, (Biolegend) was coated in 50 mm carbonate buffer, pH 9.6, at 4° C. overnight on high binding assay black plates (Costar), washed with TBST (tris buffered saline with 0.05% Tween 20) and blocked with 5% non-fat milk in TBST. Samples and standards (condition 7PA2 media) were incubated for 1.5 hr, followed by addition of 4G8 antibody [anti-Aβ residues 17-24, mouse IgG2b (Biolegend)] conjugated to horseradish peroxidase (hrp) and incubated for 1.5 hr at 25° C. After washing, ABM substrate was added, followed by detection with an absorbance plate reader.

S35 Metabolic Labeling

[$^{35}$S] metabolic labeling experiments were performed as previously described[8]. Briefly, transfected 7PA2 CHO cells were plated and treated on poly-D-lysine coated 6-well plates and metabolically labeled in DMEM-Cys/-Met (Corning CellGro, Mediatech Inc., Manassas, Va.) supplemented with glutamine, penicillin/streptomycin, dialyzed fetal bovine serum, and EasyTag EXPRESS [$^{35}$S] Protein Labeling Mix (Perkin Elmer) for 30 min. Cells were washed twice with complete media and incubated in pre-warmed DMEM for the indicated times. Media or lysates were harvested at the indicated times. Lysates were prepared in RIPA buffer (50 mM Tris [pH 7.5], 150 mM NaCl, 1% Triton X100, 0.5% sodium deoxycholate, 0.1% SDS) containing proteases inhibitors cocktail (Roche). APP species were immunopurified using protein G sepharose beads bound with 6E10 antibody, and washed four times with RIPA buffer. The immunoisolates were then eluted by boiling in 6X Laemmli buffer and separated on 12?/k SDS-PAGE. Gels were stained with Coomassie Blue, dried, exposed to phosphorimager plates (GE Healthcare, Pittsburgh, Pa.) and imaged by autoradiography using a Typhoon Trio Imager (GE Healthcare). Band intensities were quantified by densitometry in ImageQuant. Fraction secreted was calculated using the equation: fraction secreted=[extracellular [$^{35}$S]-APP signal at t/(extracellular [$^{35}$S]-APP signal at t=0+intracellular[$^{35}$S]-APP signal at t=0)]. Fraction remaining was calculated using the equation: [(extracellular [$^{35}$S]-APP signal at t+intracellular [$^{35}$S]-APP signal at t)/(extracellular [$^{35}$S]-APP signal at t=0+intracellular [$^{35}$S]-APP signal at t=0)].

CellTiterGlo Viability Assays

For determination of relative cellular ATP levels, SHSY5Y cells were seeded into flat black, poly-D-lysine coated 96-well plates (Corning). Cells were treated as indicated then lysed by the addition of CellTiter-Glo reagent (Promega). Samples were dark adapted for 10 min to stabilize signals. Luminescence was then measured in an Infinite F200 PRO plate reader (Tecan and corrected for background signal. All measurements were performed in biologic triplicate.

TMRE Staining and Flow Cytometry

Cells were treated as indicated then incubated with TMRE dye (200 nM) for 30 mins at 37° C. Samples were collected by trypsinization. Trypsin was neutralized by washing into cell culture media and then samples were washed twice in DPBS. Cell pellets were suspended into DPBS supplemented with 0.1% BSA. Fluorescence intensity of TMRE was recorded on the PE channel of a Novocyte Flow Cytometer (ACEA Biosciences, Inc.). Data are presented as mean of the fluorescence intensity from 3 experiments. For each experiment, 10,000 cells per condition in triplicates were recorded.

Example 1

High-Throughput Screen to Identify Non-Toxic IRE1 Activating Compounds

A HEK293$^{T-REx}$ cell line that stably expresses a XBP1-Renilla luciferase (XBP1-RLuc) splicing reporter was used to identify compounds that activated the IRE1/XBP1s signaling pathway[37]. Activated IRE1 selectively splices mRNA encoded by this reporter, resulting in a frame-shift that allows expression of the active Renilla luciferase enzyme[37]. The XBP1-Rluc reporter is activated by the global ER stressor thapsigargin (Tg; a SERCA inhibitor) and is blocked by co-treatment of cells with both Tg and the selective IRE1 RNAse active site inhibitor 4 µ8c.

These elements constituted an assay on a 1536-well plate format and was used to screen 646,251 compounds of the Scripps Drug Discovery Library (SDDL) at the Scripps Research Institute Molecular Screening Center (SRIMSC). In this assay, Tg exhibited a robust signal to noise ratio (4.06+/−0.23) and was used to confirm consistent assay performance across experimental plates (Z'=0.69+/−0.1). Compound dependent XBP1-RLuc activation (5.17 µM) was additionally normalized to Tg (assigned to be 100% activation) to allow comparisons between compounds across screening plates.

The primary screen identified 10,114 compounds that activated XBP1-RLuc activity >13.83% (three times the standard deviation of the negative DMSO control in the assay), representing an approximate 1.5% hit rate. From this initial group of compounds were removed compounds previously found to activate cell-based luciferase reporters of the cytosolic heat shock response.[38] Also removed were promiscuous compounds identified as positive hits in >7 assays of the SDDL. From the remaining compounds were selected the top ~6400 compounds, for which was observed compound-dependent activation of >16.36%, for triplicate confirmation screening. Toxic compounds that were found to reduce cell viability >26.19% relative to doxorubicin at the 5.17 µM screening concentration were removed, leaving 6185 non-toxic compounds showing reproducible XBP1-RLuc activation.

The next step was excluding compounds that also activated the other adaptive UPR signaling arm regulated downstream of ATF6. For this purpose, IRE1/XBP1s activation was compared for these compounds to the previously reported activation of the ATF6-selective ERSE-luciferase reporter stably expressed in HEK293$^{TREX}$ cells[37] to confirm preferential activation of the IRE1-selective XBP1-RLuc assay. Based upon these data, 640 non-toxic compounds were selected for further characterization.

Dose response curves were generated for these 640 compounds to further scrutinize compound efficacy for XBP1-RLuc activation. Compounds showed an $EC_{50}$ for XBP1-Rluc activation >3 µM and maximal activity <20% relative to Tg activation were removed. Iterative chemical subclustering of these primary hits yielded a representative set of 128 compounds that reflects the diversity and relative abundance of structurally similar scaffolds among these top hits (FIG. 1). The two most represented groups in this analysis were Cluster "H" containing an aryl sulfonamide moiety and Cluster "A" containing a N1-phenyl substituted pyrazolopyrimidine substructure. These structures are commonly found in compounds that bind active sites of protein kinases: these could activate IRE1 by binding the nucleotide binding pocket of the kinase domain[39]. Because the present disclosure is focused upon identification of compounds that activate IRE1 independent of this mechanism, compounds in Clusters A and H were excluded from consideration. From the remainder were selected 7 compounds that represent 5 different structural classes: these are compound Nos. 198, 202, 291, 474, 939, 967, and 970, as shown herein.

Example 2

Compounds Promote IRE1-Dependent XBP1s Activation

Figure 2A:
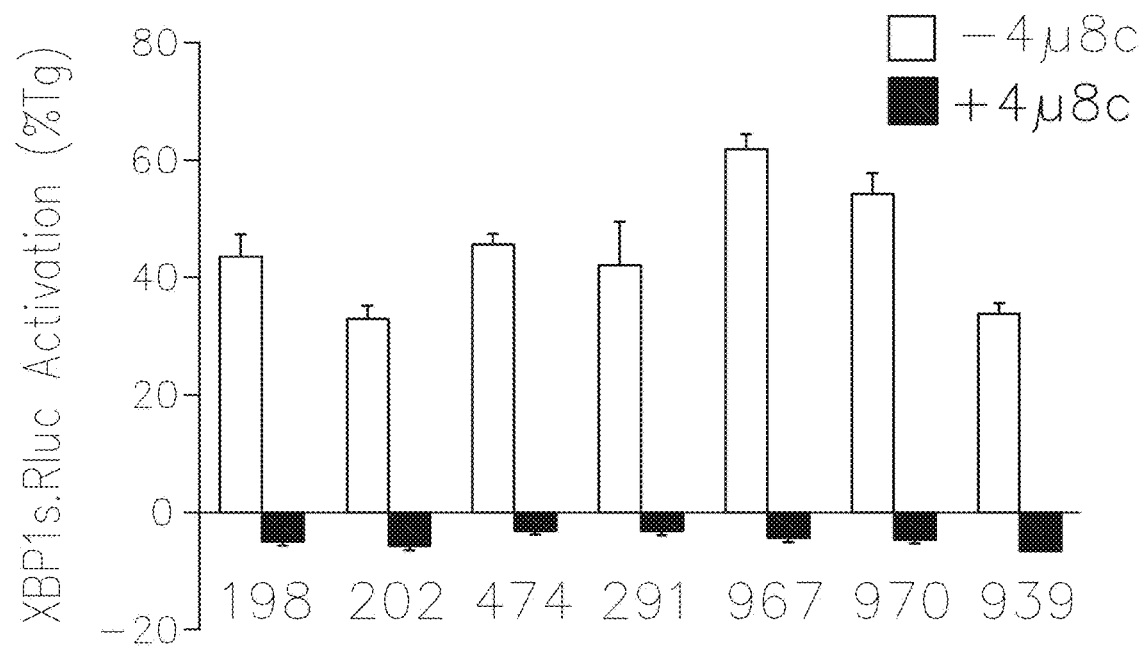
FIG. 2A and FIG. 2B. Activation of RLuc luminescence in HEK293T-Rex cells stably expressing XBP1s-RLuc treated with 10 µM IRE1 activators in the presence or absence of IRE1 inhibitor 4 µ8c (32 µM) for 18 hr. Luminescence is shown as % signal relative to Tg treatment (500 nM; 18 hr). Error bars represent standard deviation for n=3 replicates (FIG. 2A), Activation of RLuc luminescence in HEK293T-Rex cells stably expressing XBP1s-RLuc treated with the indicated concentrations of IRE1 activator compounds for 18 hr. Luminescence is shown as % signal relative to Tg treatment (500 nM; 18 hr) Error bars represent standard deviation for n=3 replicates (FIG. 2B).
Figure 2B:
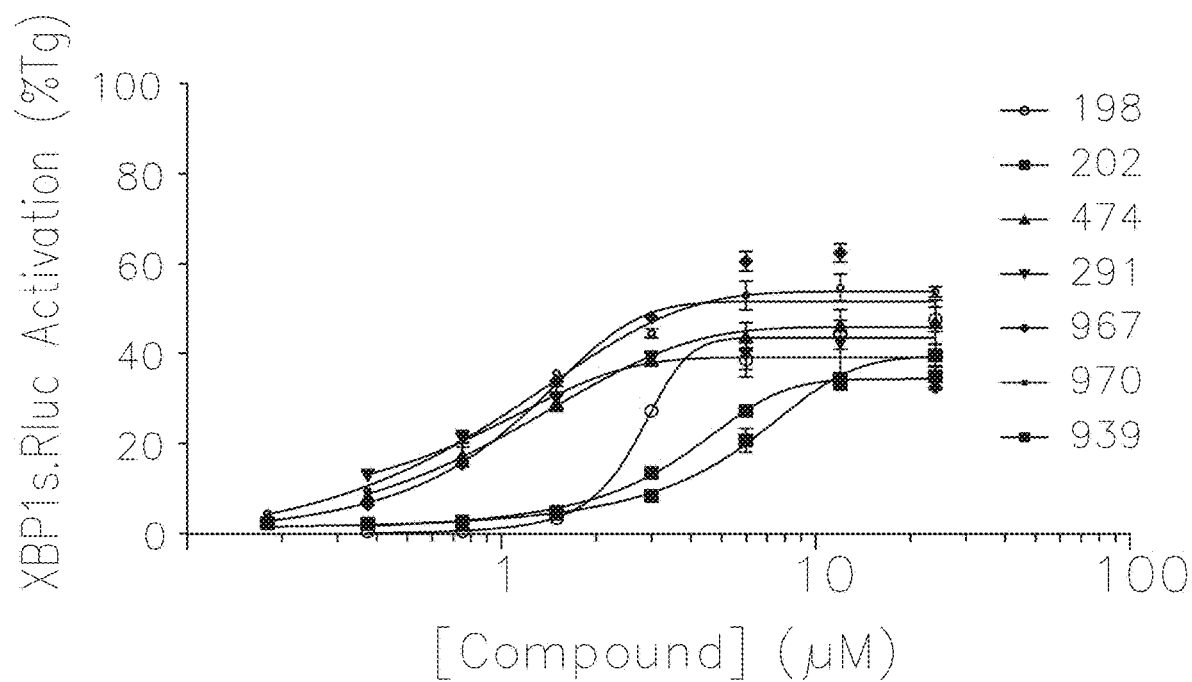

The compounds from Example 1 exhibited concentration-dependent activation of XBP1-RLuc in HEK293$^{TREX}$ cells, demonstrating maximal reporter activation to levels 35-50% of that observed with the global ER stressor Tg with $EC_{50}$'s between 1-3 µM (FIG. 2A and FIG. 2B). Both results were consistent with those observed during high-throughput screening. These data confirm that co-administration of the compounds with the IRE1 active site inhibitor 4 µ8c blocked compound-dependent activation of the XBP1 splicing reporter (FIG. 2A), support the conclusion that the compounds activate this reporter through an IRE1-dependent mechanism.

Figure 3A:
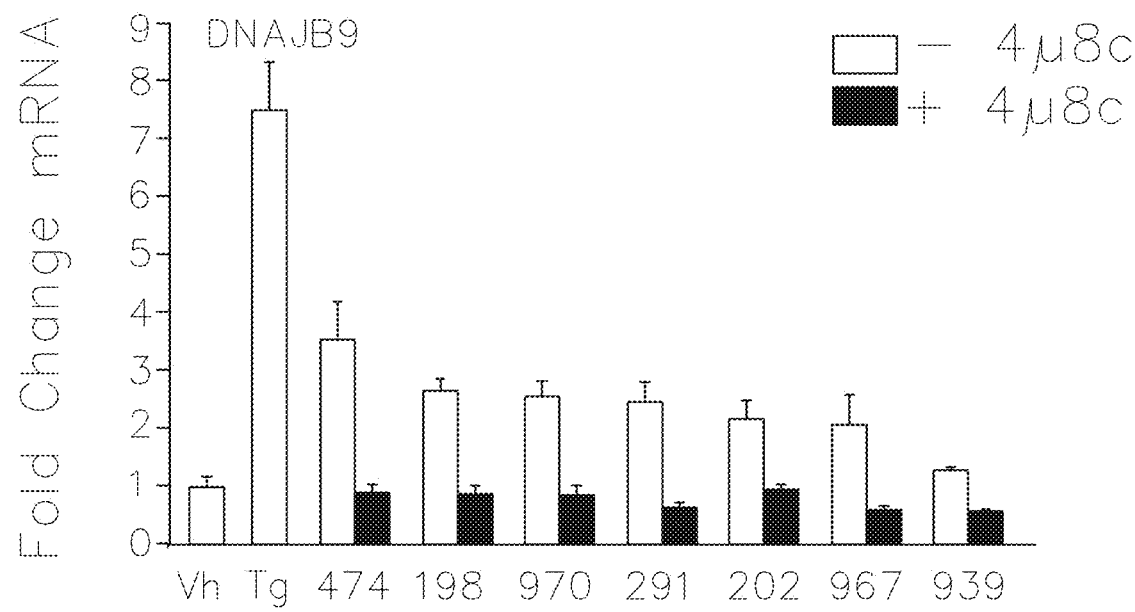
FIG. 3A-FIG. 3D. Graph showing qPCR analysis of the XBP1 target gene DNAJB9 in HEK293T cells treated for 4 h with IRE1 activator compounds (10 µM), or Tg (500 nM), in the presence or absence of 4 µ8c (32 µM). Error bars show SEM for n=3. P-values calculated using one-tailed Student's t-test (FIG. 3A). Graph showing qPCR analysis of the XBP1 target gene CHOP in HEK293T cells treated for 4 h with IRE1 activator compounds (10 µM), or Tg (500 nM), in the presence or absence of 4 µ8c (32 µM). Error bars show SEM for n=3. P-values calculated using one-tailed Student's t-test (FIG. 3B). Graph showing qPCR analysis of the XBP1 target gene BiP in HEK293T cells treated for 4 h with IRE1 activator compounds (10 µM), or Tg (500 nM), in the presence or absence of 4 µ8c (32 µM). Error bars show SEM for n=3. P-values calculated using one-tailed Student's t-test (FIG. 3C). Western blot of IRE1 following Phos-tag SDS PAGE to separate phosphorylated and unphosphorylated IRE1 in HEK293T cells treated with 10 µM compound 198, 474, or 970 or 1 µM APY29 in the presence or absence of 500 nM Tg for 4 hours (FIG. 3D).

The compounds were next evaluated for their abilities to induce expression of the IRE1-selective target gene DNAJB9 (also known as ERdj4) in HEK293T cells using qPCR. This gene is primarily regulated by IRE1/XBP1s signaling in these cells as evidenced by the fact that Tg-dependent increases in DNAJB9 are suppressed by co-treatment with the IRE1 inhibitor 4 µ8c. The compounds increase the expression of DNAJB9 in these cells to levels 30-50% of those observed in Tg-treated cells (FIG. 3A), mirroring the levels of activation observed by our reporter assay (FIG. 2A). The increased DNAJB9 expression was inhibited in cells co-treated with the IRE1 active site inhibitor 4 µ8c, confirming that this effect is dependent on IRE1. (FIG. 3A). These results demonstrate that the compounds activate IRE1 activity to levels 30-50% those observed following global Tg-dependent ER stress.

Figure 3B:
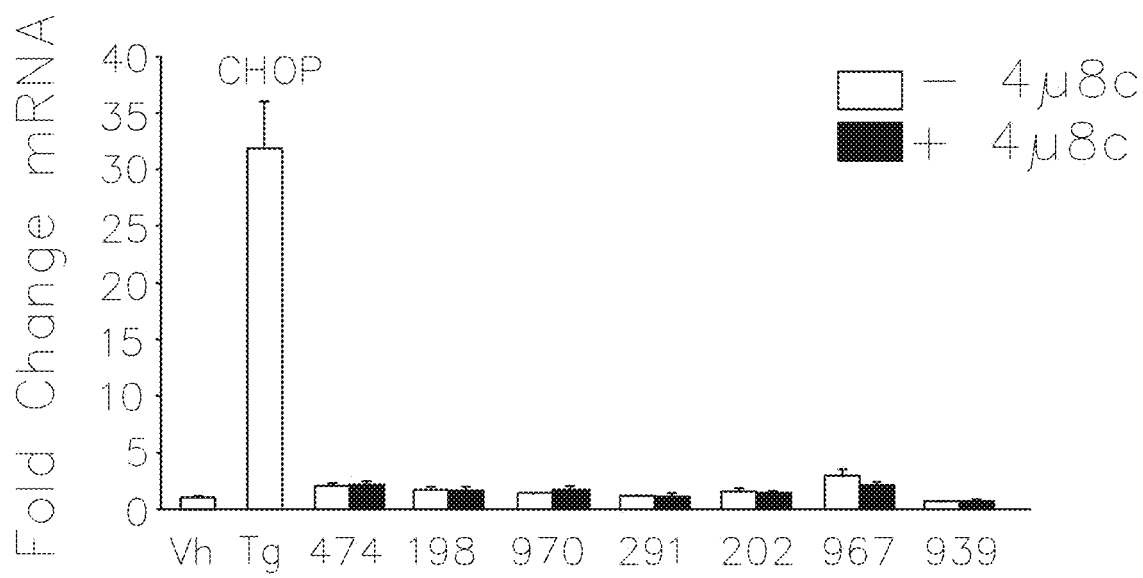
Figure 3C:
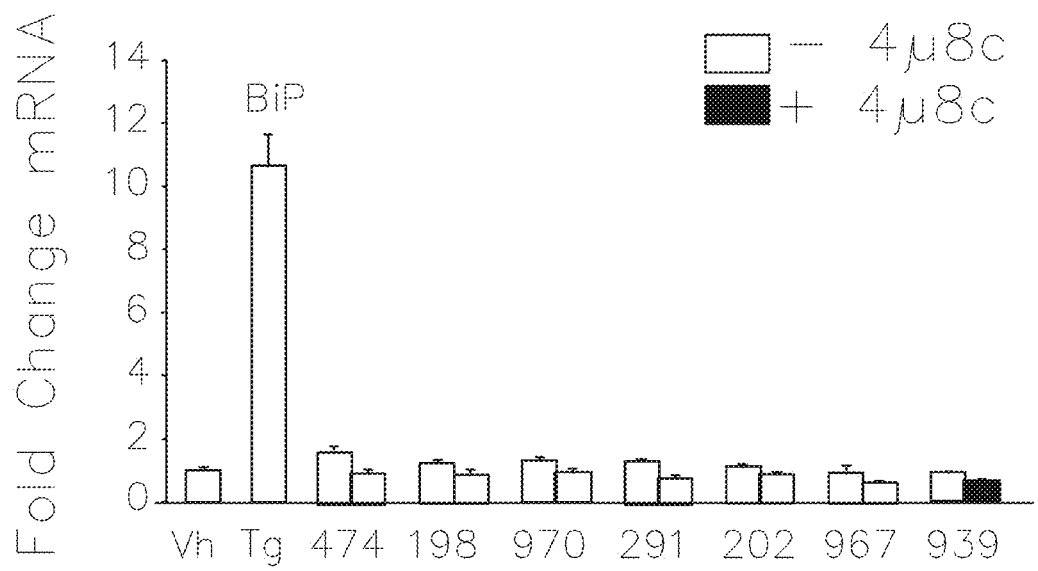

The compounds were measured for their abilities to induce expression of ER stress-responsive genes CHOP and BiP (or WAS) regulated downstream of the PERK and ATF6 UPR signaling pathways, respectively[8, 40]. The Tg-dependent expression of these two genes is largely insensitive to 4 µ8c, confirming their induction through an IRE1/XBP1s independent mechanism. The compounds did not significantly induce CHOP in HEK293T cells (FIG. 3B). A modest compound-dependent increase in B/P expression was observed—an ER stress-responsive gene primarily regulated by the ATF6 UPR signaling pathway[8] (FIG. 3C), However, this increase was blocked by co-treatment with 40c, demonstrating that this increase reflects the modest BiP expression previously observed upon chemical genetic XBP1s activation[8] (FIG. 3C). Collectively, these results support the conclusion that the compounds selectively activate IRE1 XBP1s signaling independent of other UPR signaling pathways.

Compounds 474, 198, and 970 were selected as exemplary hits based on their selective IRE1-depedendent induction of DNAJB9, their $EC_{50}$ of XBP1-RLuc activation of <3 µM and their high maximal activation of IRE1signaling measured by both XBP1s-RLuc activity and DNAJB9 expression (>50% that observed with Tg). These compounds increased IRE1-dependent XBP1splicing in wild-type mouse embryonic fibroblast (MEF) cells. However, this splicing was not observed in Ire1-deficient MEF cells, further confirming that these compounds increase XBP1 splicing by an IRE1-dependent mechanism.

Example 3

Compound-Dependent IRE1 Activation Requires IRE1 Autophosphorylation

Figure 3D:
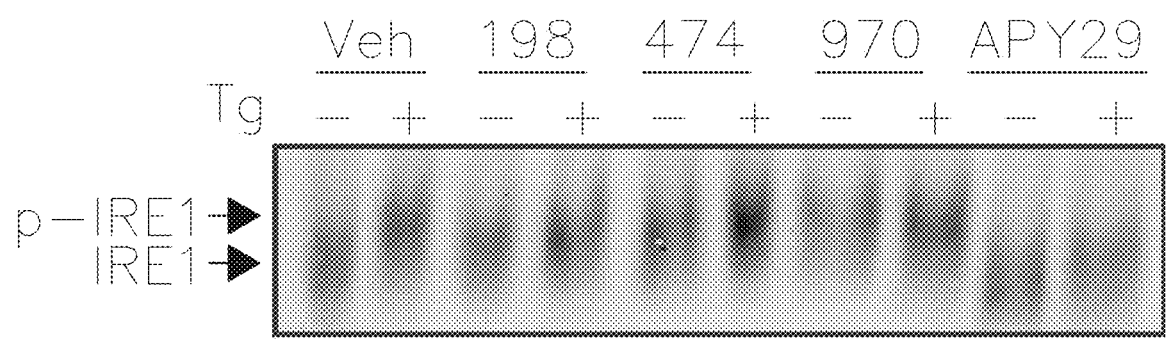

Compounds that activate IRE1 through binding the IRE1 kinase active site and inhibiting IRE1 autophosphorylation can elicit off-target activity likely associated with binding to other protein kinases.[20, 35, 36] Thus, the purpose of this example was to define the dependence of the present compounds on IRE1 kinase activity. HEK293T cells were treated with compound 198, 474, or 970 in the absence or presence of Tg, and IRE1 phosphorylation was monitored by using Phos-tag SDS-PAGE and immunoblotting. As a control, cells were treated with APY29—an IRE1 kinase site inhibitor that allosterically activates the IRE1 RNAse[20] in the absence or presence of Tg. Cells treated with a test compound alone increased phosphorylated IRE1 (FIG. 3D). In contrast, co-treatment of Tg and APY29 showed significant reductions in IRE1 phosphorylation, reflecting the inhibition of IRE1 kinase activity afforded by this compound[20] (FIG. 3D). These results indicate that the compounds do not inhibit IRE1 kinase activity, but instead they promote IRE1 autophosphorylation.

Next was determined the dependence of compound-dependent IRE1 RNAse activation on autophosphorylation. HEK293T cells were initially treated with the compounds in the absence or presence of KIRA6—a compound that binds the nucleotide binding pocket and inhibits both IRE1 kinase and RNAse activity[36]. Co-treatment with KIRA6 blocked compound-dependent XBP1splicing. This result indicates that pharmacologic inhibition of IRE1 kinase activity prevents IRE1 activation that is afforded by the compounds disclosed herein.

Figure 4:
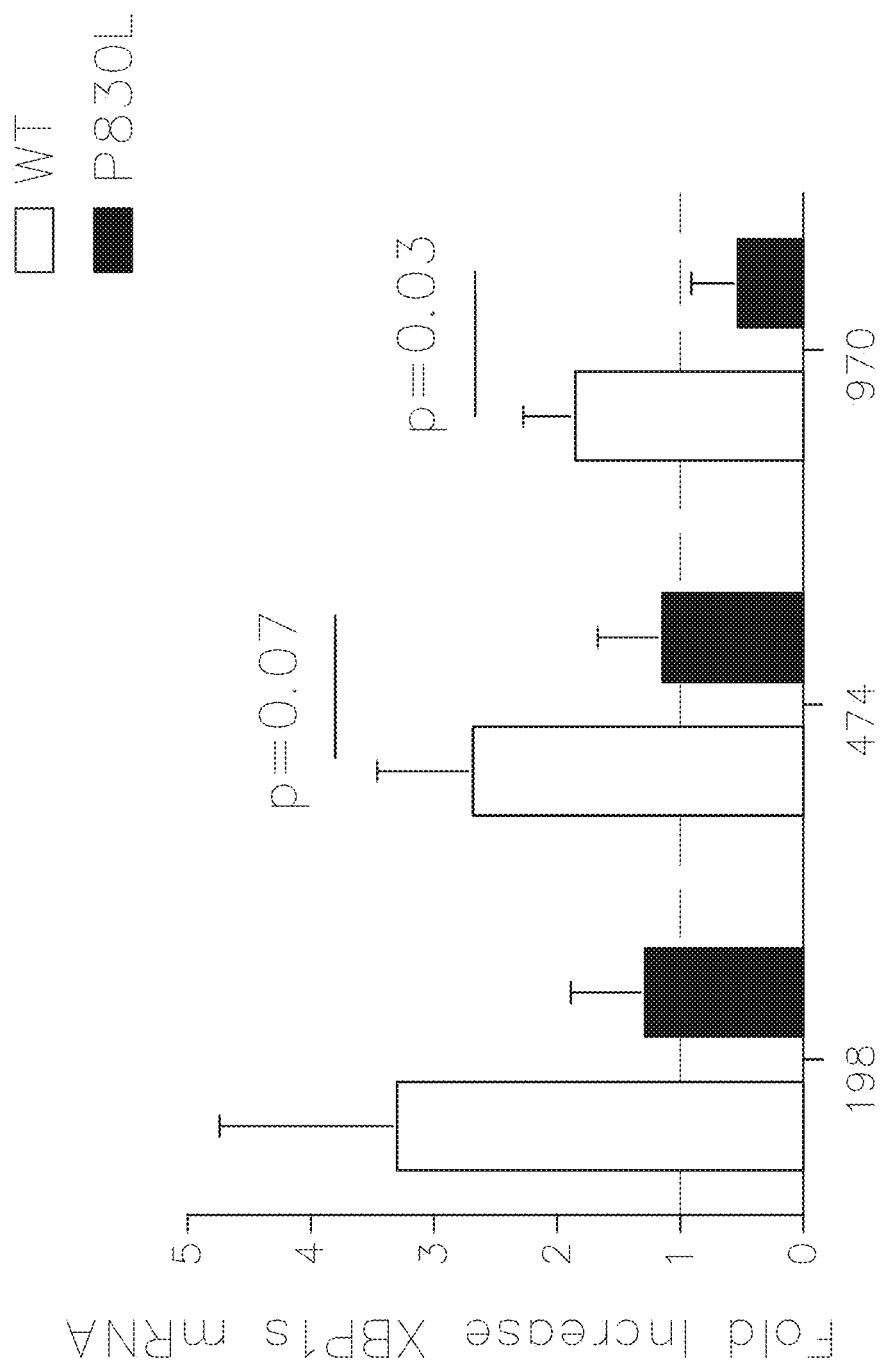
FIG. 4. qPCR of XBP1s mRNA levels in IRE1 KO MEF cells reconstituted with WT or P830L IRE1, treated with 10 µM 198, 474, 970, or 500 nM Tg for 4 hours. Error bars represent SEM for n=replicates.

We next monitored the appearance of XBP1s mRNA in Ire1-deficient MEF cells reconstituted with IRE1$^{WT}$ or the kinase-inactive P830L IRE1 mutant[41] by qPCR. It was found that genetic disruption of IRE1 kinase activity blocked compound-dependent IRE1 activation (FIG. 4). Collectively, these results demonstrate that the compounds activate IRE1/XBP1s signaling through a mechanism requiring IRE1phosphorylation. The results further support the conclusion that the compounds do not bind the IRE1 kinase active site, which binding can limit off-pathway activity associated with binding other protein kinases.

Example 4

Compounds 474 and 970 Selectively Activate the IRE1/XBP1s UPR Signaling Pathway

The purpose of this example was to define the ability of the compounds to selectively induce expression of IRE1/XBP1s target genes: for this purpose, RNAseq was performed on HEK293T cells that had been treated with compound No. 198, 474, or 970 for 6 h. As a control, RNAseq was performed on cells that had been treated with the global UPR activator Tg. The majority of genes that are significantly induced by the compounds are known transcriptional targets of IRE1/XBP1s signaling. These include the ER stress-responsive transcription factor XBP1 and the ER proteostasis factors SEC24D, DNAJB39, and HERPUD1[8].

The next step defined the selectivity of the compounds for IRE1/XBP1s signaling relative to other arms of the UPR. This was accomplished by monitoring the expression of established genesets comprised of 10-20 genes that are preferentially induced by the IRE1/XBP1s, ATF6, or PERK UPR signaling pathways[8, 42]. A notable challenge with this analysis is the comparison of gene expressions that are induced to different extents through activation of these three UPR signaling pathways (e.g., ATF6 target genes are generally induced more than IRE1/XBP1s target genes)[8]. To overcome this challenge, the expression of individual genes that are included in these genesets were normalized to the expression observed in Tg-treated cells (Tg representing 100% activation of these genes). It was therefore possible to directly compare gene expression without complications arising from differential expression[42].

By this approach it was found that all three compounds activate the IRE1/XBP1s geneset to levels 30-40% that observed for Tg levels nearly identical to those observed using XBP1-RLuc activation or DNAJB39 expression as described above. The compounds showed only a modest increase in the activation of the ATF6 target geneset (<20% that observed with Tg), which is consistent with previous reports reflecting overlap between numerous genes primarily regulated by ATF6 and their mild induction by IRE1/XBP1s (e.g., BiP)[8]. Thus, these results indicate that the compounds do not significantly activate ATF6 transcriptional signaling. However, compound 198 increased expression of the PERK geneset, indicating that this compound mildly activates the PERK-regulated transcriptional program. Compounds 474 and 970 did not demonstrate this effect. Collectively, these results indicate that compounds 474 and 970 preferentially activate the IRE1/XBP1s signaling arm of the UPR, while compound 198 shows some potential off-pathway activity.

Also evaluated was IRE1 RIDD activity induced by the compounds using the RNAseq dataset. Despite robust IRE1/XBP1s transcriptional activity following 6 hours of treatment, there was no evidence for RIDD after the same 6 hours. There was also no significant reductions in the well-established RIDD targets SCARA3, Bloc1s1 and Col6A1 at this timepoint, although the levels of these mRNA are reduced in Tg-treated cells. Taken together, these results indicate that the compounds promote adaptive IRE1/XBP1s signaling, but not RIDD on this short time scale.

Example 5

IRE1/XBP1s Activating Compounds Promote Targeted ER Proteostasis Reprogramming

The purpose of this example is to demonstrate how transcriptional profiling data defined the global impact of the compounds in HEK293T cells. Gene Ontology (GO) analysis showed that compounds 198, 474 and 970 primarily induce expression of genes annotated with GO terms related to ER stress and the UPR. The analysis demonstrates that the compounds do not globally influence non-UPR signaling pathways. Furthermore, application of an established geneset approach similar to that described Example 4 demonstrated that the compounds do not significantly activate stress-responsive signaling pathways responsible for regulating proteostasis in other cellular environments such as the cytosolic heat shock response, the oxidative stress response, or other pathways including the mitochondrial unfolded protein response and the NFκB inflammatory response in HEK293T cells[42]. These results support the conclusion that compounds 474 and 970 (and to a lesser extent 198), as examples of the compounds described herein, do not significantly activate other stress responsive signaling pathway apart from IRE1/XBP1s.

The selectivity of the compounds for IRE1/XBP1s was further characterized by comparing (a) the expression of the top 100 genes significantly induced in compound-treated HEK293T cells to (b) the expression of these genes following stress-independent XBP1s or ATF6 activation in HEK293$^{DAX}$ cells. These cells stably express both doxycycline (dox)-inducible XBP1s and trimethoprim (TMP) regulated DHFR.ATF6, allowing stress-independent activation of XBP1s and/or ATF6 signaling through addition of the activating ligands dox or TMP, respectively[8]. It was found that the majority of the top 100 genes induced by compounds 474 and 970 overlapped with genes induced by dox-dependent XBP1s activation; as expected, dox-dependent XBP1s activation induces these genes to higher extents. The high level of overlap observed for genes induced by dox-dependent XBP1s and 474 or 970 is further evident when comparing the number of genes significantly induced >1.2 fold by either compound treatment or dox-dependent XBP1s activation: compound 474 shows >80% overlap of genes induced >1.2 fold, while compound 970 shows >60% overlap, with most non-overlapping genes showing only mild induction (<1.3-fold) in 970-treated cells. In contrast, compound 198 shows less overlap with dox-dependent XBP1s activation, reflecting the more promiscuous nature of this compound in comparison to other IRE1 activators. These results demonstrate that 970 and especially 474 show selectivity for IRE1 activation within HEK293T cells.

One of the mechanisms by which IRE1/XBP1s activation is protective is through the targeted transcriptional remodeling of ER proteostasis pathways. Because it was observed that compounds such as 474 and 970 selectively activate IRE1/XBP1s signaling, it was desired to confirm that these compounds similarly promote targeted ER proteostasis network remodeling. Thus, the RNAseq data set described above was utilized to compare the expression of 124 proteostasis factors (including chaperones, degradation factors, PDIs, and trafficking factors) that localize to different intracellular environments in cells treated with IRE1 activating compounds 970 or 474. It was found that these IRE1/XBP1s activators induce selective remodeling of the ER proteostasis factors relative to other compartments.

Quantitative immunoblotting against XBP1 as well as the IRE1/XBP1s-regulated ER trafficking factor Sec24D confirmed that changes in gene expression correspond with alterations in protein expression. These results demonstrate that the compounds (e.g., 474) induce adaptive remodeling of ER proteostasis pathways through selective activation of the IRE 1/XBP1s signaling pathway.

Example 6

Pharmacologic IRE1 Activation Reduces Secretion of Amyloid Precursor Protein (APP) and Aβ

The purpose of this example is to show that the compounds described herein are useful for correcting pathologic imbalances in ER proteostasis for disease-relevant proteins such as amyloid precursor protein (APP). APP is a secretory protein that undergoes proteolytic processing by multiple proteases to produce aggregation-prone cleavage products including the secreted amyloidogenic peptide Aβ[44]. (Previous results show that enhancing ER proteostasis could reduce production of toxic Aβ in conditioned media)[31].

Figure 5A:
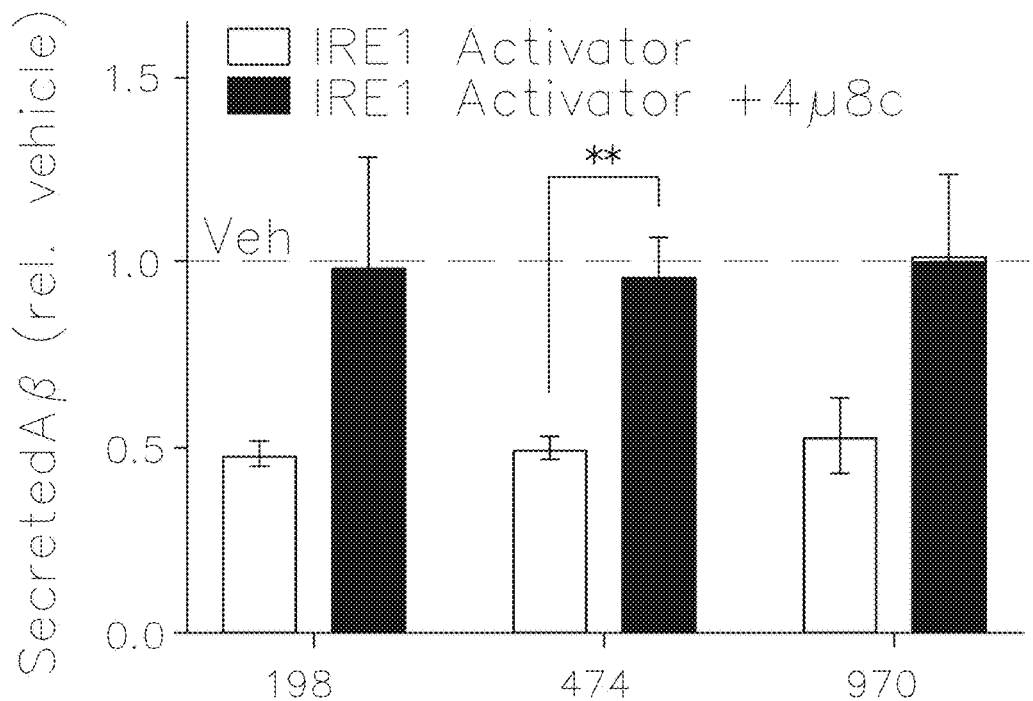
FIGS. 5A-5D. Graph showing relative signal from ELISA assay of secreted Aβ peptide from conditioned media prepared on 7PA2 CHO cells treated with IRE1 activators 198, 474, or 970 (10 µM) in the presence or absence of 4 µ8c (32 µM). Cells were treated for 18 hours, media was then replaced and conditioned in the presence of treatments for 24 hours before harvesting for ELISA assay. Error bars represent SEM for n=3 replicates. Statistics calculated from one-tailed Student's t-test. *p<0.05, p<0.01, *p<0.001 (FIG. 5A). Quantification of media and lysate immunoblots from 474 treatment (10 µM) of APP. Error bars represent Standard Deviation for n=3 replicates. Statistics calculated from one-tailed Student's t-test. *p<0.05, p<0.01 *p<0.001 (FIG. 5B). Plot showing fraction of total remaining APP at each time point after S35 metabolic labeling of newly synthesized protein, accounting for the sum of APP in lysate and media. Error bars represent Standard Deviation for n=3 replicates. Statistics calculated from one-tailed Student's t-test. *p<0.05, p<0.01, *p<0.001 (FIG. 5C). Plot showing fraction of secreted APP collected at 2 hours after metabolic labeling. Error bars represent Standard Deviation for n=3 replicates. Statistics calculated from one-tailed Student's t-test. *p<0.05, p<0.01, *p<0.001 (FIG. 5D).

ELISA was used to monitor Aβ in media conditioned on a CHO cell line stably expressing the destabilized, disease-associated V717F APP mutant (CHO$^{7PA2}$)[45] treated with or without compounds 198, 474, and 970. All three compounds reduced Aβ in conditioned media to levels 50% of those observed in control conditioned media (FIG. 5A). In contrast, the compounds did not significantly influence CHO$^{7PA2}$ viability, demonstrating that the reduced Aβ secretion cannot be attributed to cell death. The reduction in A secretion can be attributed to IRE1 activation because the reduced extracellular accumulation of Aβ is blocked by co-treatment with the active site IRE1 inhibitor 4 μ8c (FIG. 5A). Pharmacologic IRE1 activation with the compounds also reduced extracellular Aβ in media conditioned on CHO$^{7WD10}$ cells stably expressing wild-type APP (APP$^{WT}$) without impacting cellular viability.

Figure 5B:
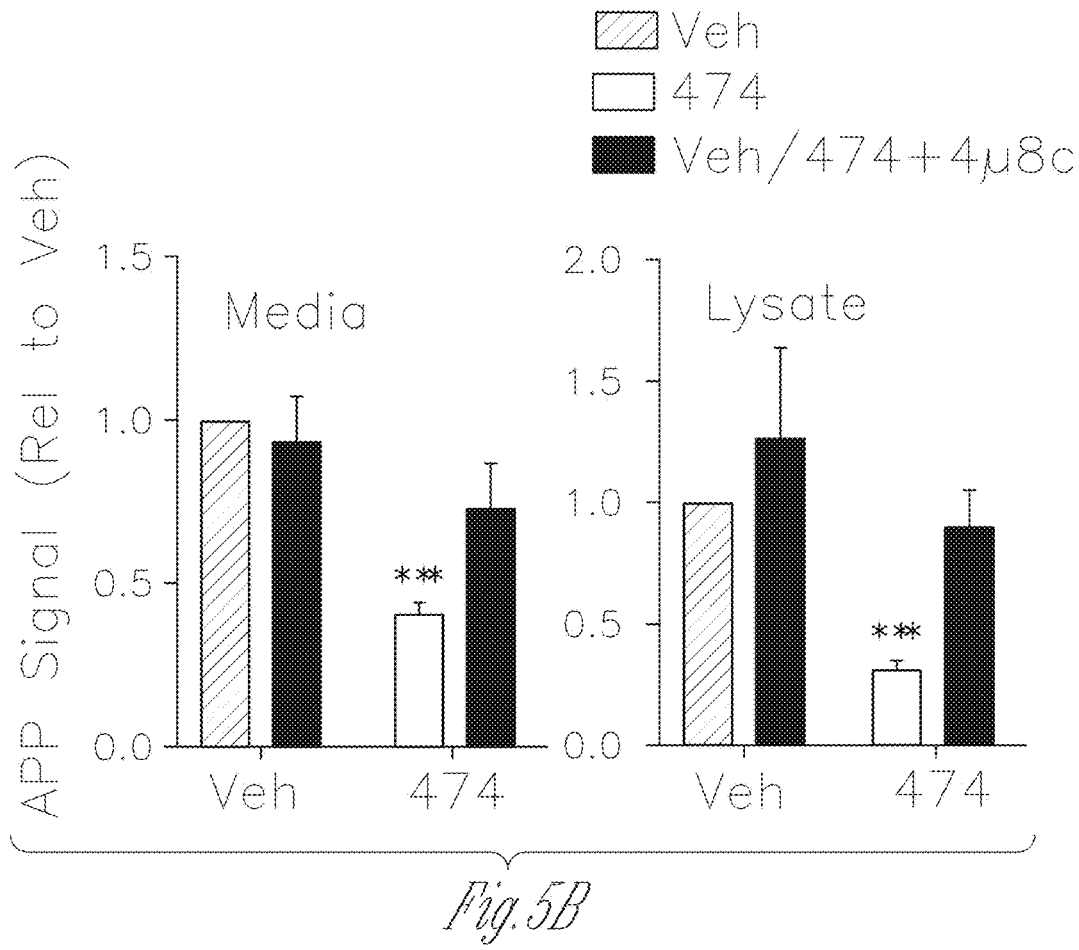

Further, CHO$^{7PA2}$ cells treated with compound 474 showed reduced APP levels in both lysates and conditioned media, supporting the conclusion that the compound increased APP degradation (FIG. 5B). This result could be reversed by co-treatment with 4 μ8c. Similar results were observed for other representative compounds, such as compound 198.

Figure 5C:
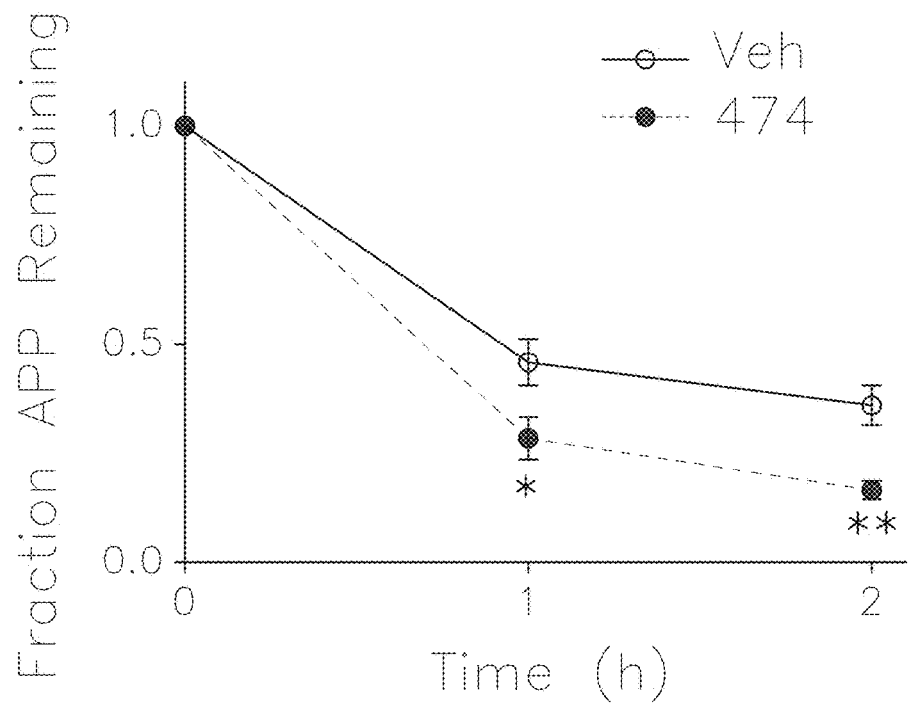
Figure 5D:
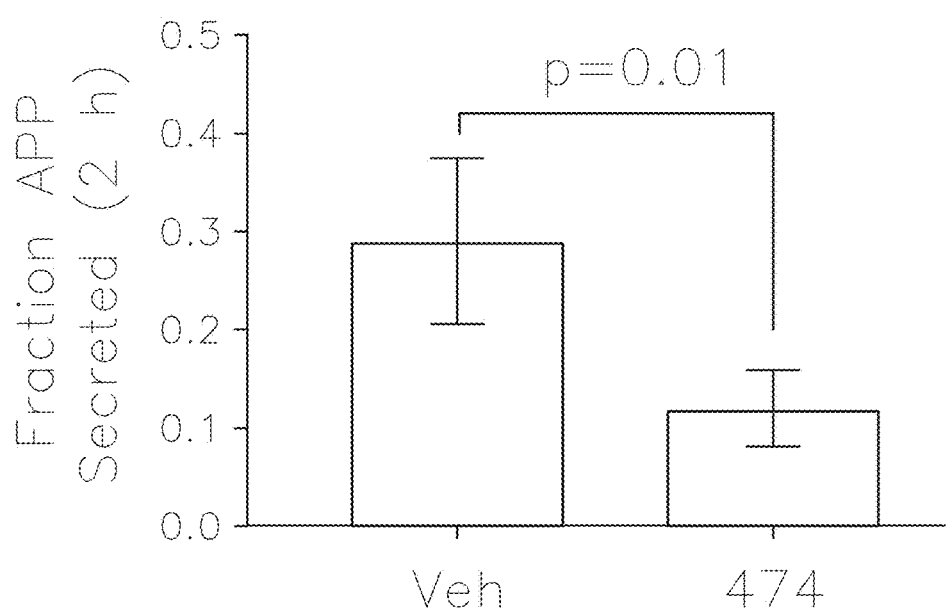

[$^{35}$S] metabolic labeling confirmed that treatment with 474 and other IRE1 activators reduced the secretion of soluble APP into the media and increased APP degradation (FIG. 5C, FIG. 5D). Similar results were observed with additional IRE1 activators including 198 and 970. Collectively, these results demonstrate that pharmacologic IRE1/XBP1s activation mimics alterations in APP ER proteostasis previously observed upon XBP1s overexpression[31].

Example 7

IRE1 Activation Prevents Mitochondrial Dysfunction Induced by Mutant APP Overexpression The purpose of this example is to show that enhanced APP ER proteostasis afforded by pharmacologic IRE1 activation mitigates cellular toxicity that is associated with the expression of this destabilized, disease-associated protein. Previous results show that overexpression of APP$^{WT}$ or the Swedish APP (APP$^{SW}$) double mutant (K595N/M596L) protein induces mitochondrial depolarization in SHSY5Y neuroblastoma cells, in a manner linked to APP species localized to mitochondria and mitochondria-associated endoplasmic reticulum membranes (MAMs)[46, 47]. Consistent with these results, it was found that overexpression of APP$^{WT}$ or APP$^{SW}$ in SHSY5Y resulted in a 25% and 40% reduction of mitochondrial membrane potential, respectively, as measured by staining with tetramethylrhodamine (TMRE) and FACS sorting.

Figure 6A:
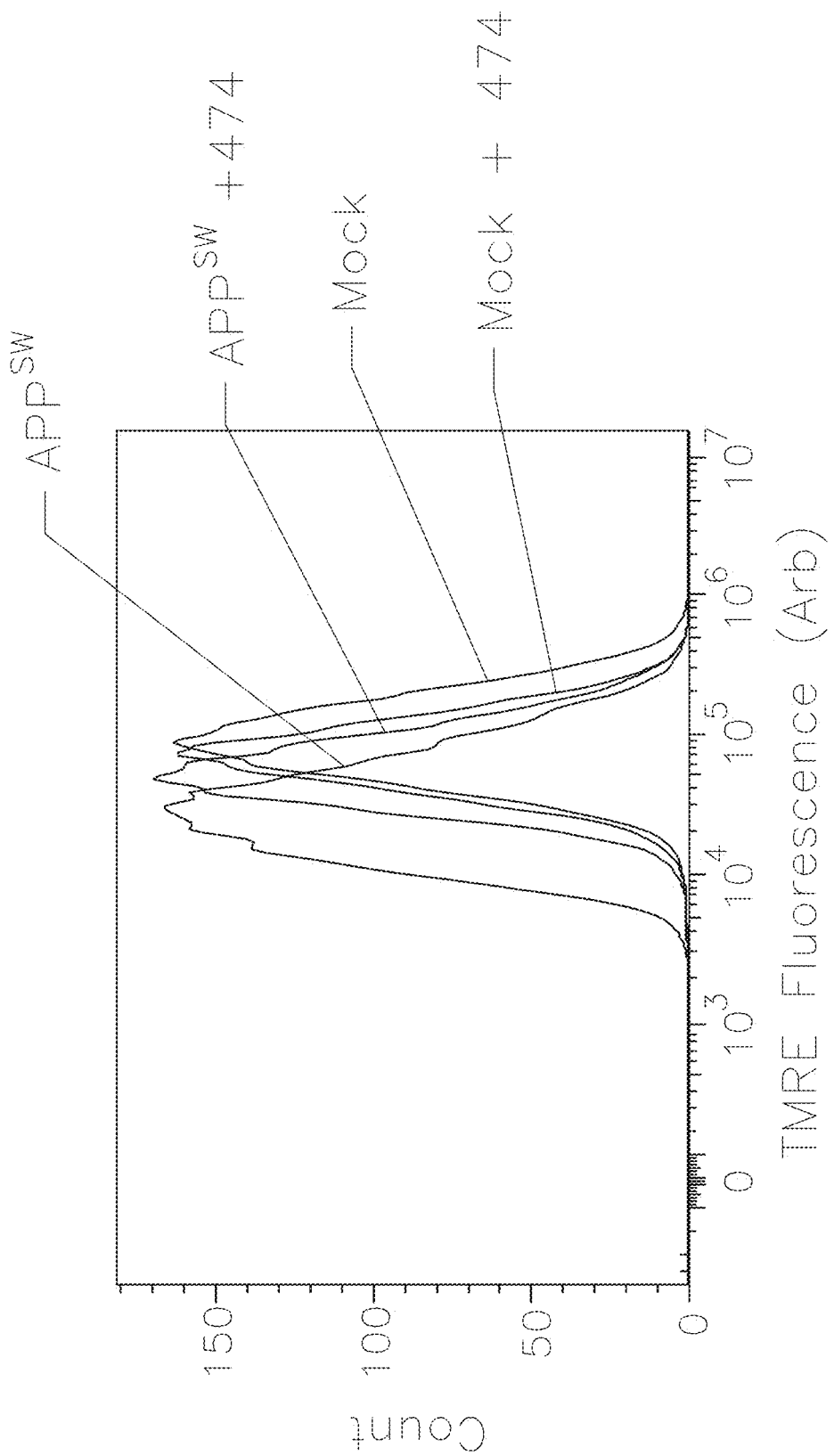
FIGS. 6A-6C. Histograms showing TMRE staining of SH-SY5Y cells transiently expressing empty vector (Mock) or Swedish mutant APP in the presence or absence of 474 (10 µM) for 72 hours (FIG. 6A). Quantification of TMRE staining in (A). Error bars represent SEM for n=3 replicates. Statistics calculated from one-tailed Student's t-test. *p<0.05, p<0.01, *p<0.001 (FIG. 6B). Graph showing relative luminescence from CellTiterGlo assay of SH-SY5Y cells transiently expressing empty vector or Swedish mutant APP cultured in galactose media for 72 hours in the presence or absence of IRE1 activator 474 (10 µM). Error bars represent SEM for n=3 replicates. Statistics calculated from one-tailed Student's t-test. *p<0.05, p<0.01, *p<0.001 (FIG. 6C).
Figure 6B:
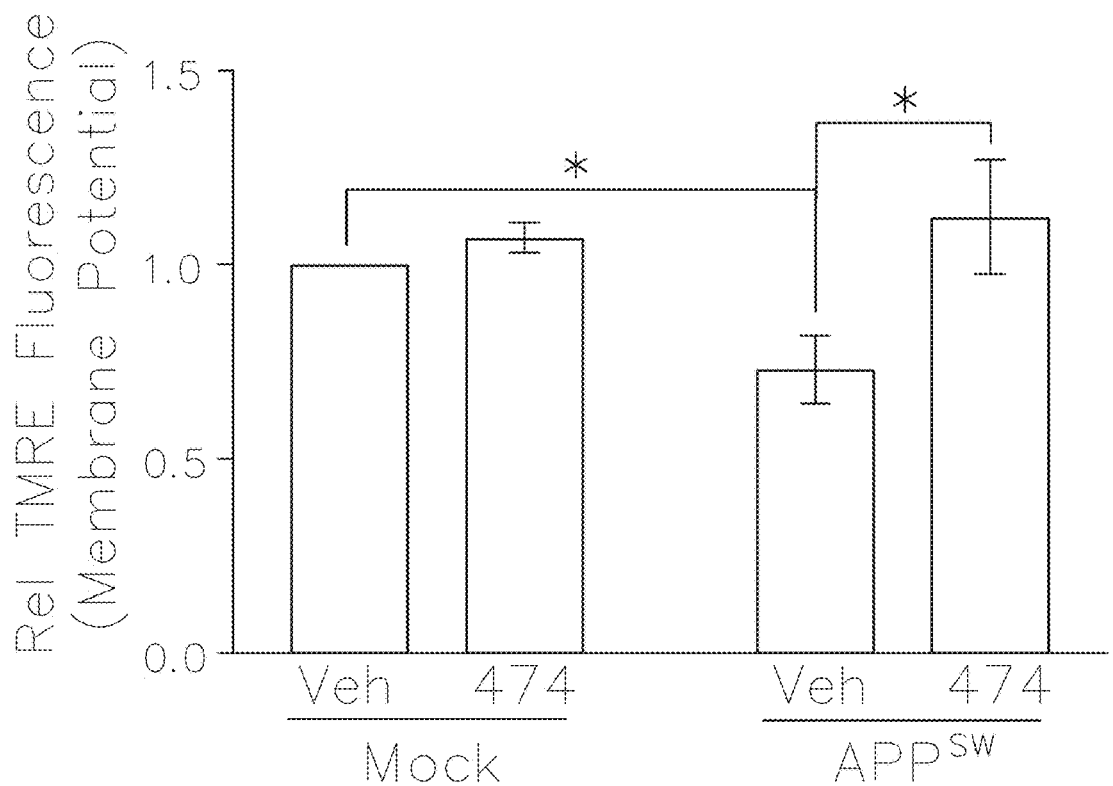

Overexpression of APP$_{SW}$ in SHSY5Y cells modestly increased expression of the IRE1/XBP1s target gene DNAJB9 and the ATF6 target gene BiP, but not induced the PERK-regulated target gene CHOP. Treating these cells with compound 474 further increased DNAJB9 expression and thereby confirmed compound activity. Next, mitochondrial membrane potential was monitored in SHSY5Y cells overexpressing APP$^{SW}$ and that had been treated with 474. On its own, 474 did not influence mitochondrial membrane potential in mock-transfected cells (FIG. 6A,B). However, treatment with 474 prevented APP$^{SW}$-associated reductions in mitochondrial membrane potential. Similar results were observed in cells overexpressing APP$^{WT}$ in SHSY5Y cells.

Mitochondrial depolarization decreases the capacity for cells to produce ATP through oxidative phosphorylation at the inner mitochondrial membrane. Thus, a further purpose of this example is to show that AP$^{SW}$-dependent mitochondrial depolarization induces an energy imbalance through reduced mitochondrial ATP production. Accordingly, ATP levels were monitored in SHSY5Y cells overexpressing APP$^{SW}$ and incubated in media that was supplemented with glucose or galactose. APP$^{SW}$ overexpression did not significantly influence ATP levels in cells cultured in glucose, consistent with the primary dependence of these cells on glycolysis for ATP production[48].

Figure 6C:
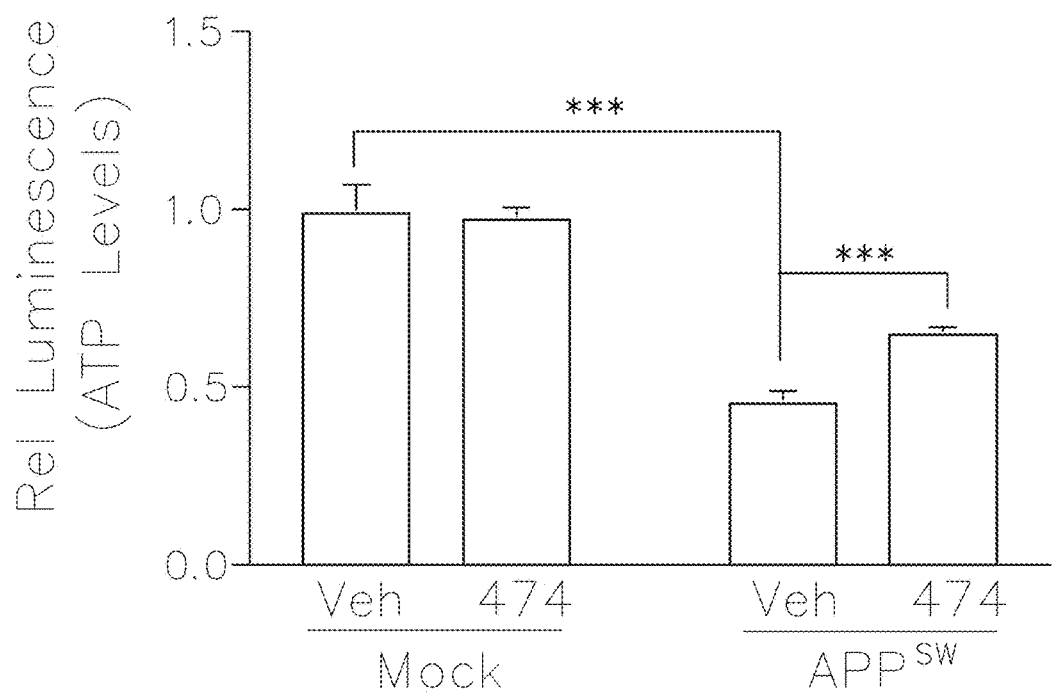

In contrast, APP$^{SW}$ overexpression in cells cultured in galactose resulted in significant reductions in ATP levels, reflecting the increased dependence of these cells on mitochondria for ATP production. Treating cells with 474 increased. ATP levels in APP$^{SW}$ overexpressing cells that were cultured in galactose (FIG. 6C). The results further support the conclusion that pharmacologic IRE1 activation ameliorates toxic mitochondrial dysfunction that is induced by overexpression of APP$^{SW}$ mutant.

Example 8

Pharmacologic IRE1 Activation for Treating Type 2 Diabetes

Figure 7A:
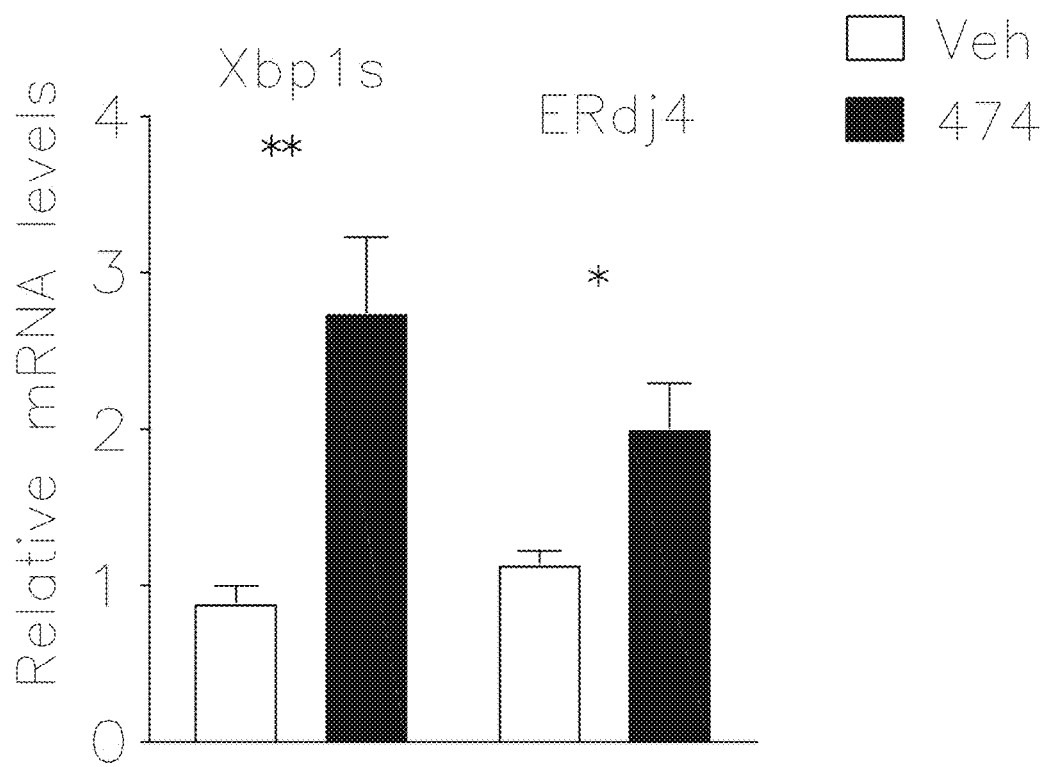
FIGS. 7A-7D. RT-PCR of Xbp1s and the IRE1/XBP1s target gene Erdj4 from adipose tissue post single IP dose of 474 (FIG. 7A). Liver RNAseq profiles of ATF6, IRE1 and PERK target genes expressed as log 2 fold change of chronic 474 treatment compared to vehicle (FIG. 7B). Body weight (FIG. 7C) and food intake (FIG. 7D) over 6 weeks of dosing.

Obesity has grown into a major public health crisis over the past few decades, enhancing the risk of numerous complications such as type 2 diabetes (T2D). Recent studies have established a close link between the ER stress response, most notably the IRE1 pathway, and insulin resistance associated with T2D[33]. Haploinsufficiency of Xbp1, the key transcription factor downstream of IRE1, causes insulin resistance through increased accumulation of ER stress[33]. Conversely, overexpression of active Xbp1s in the livers of ob/ob mice restores insulin signaling and reduces gluconeogenesis through the targeted degradation of a key metabolic regulator, FoxO1[55]. IRE1 function is also critical in the maintenance of pancreatic β-cell function and glucose stimulated-insulin secretion[56]. Although these genetic studies highlight the therapeutic potential of targeting the IRE1-XBP1s signaling axis for T2D and related metabolic disorders, no highly-selective pharmacological IRE1 activators have been available until the present disclosure's provision for screening and optimization of a lead molecule, 474. Compound 474 is readily bioavailable after a single IP dose, as indicated by the induction of IRE1-specific target genes in adipose tissue (FIG. 7A).

Figure 7B:
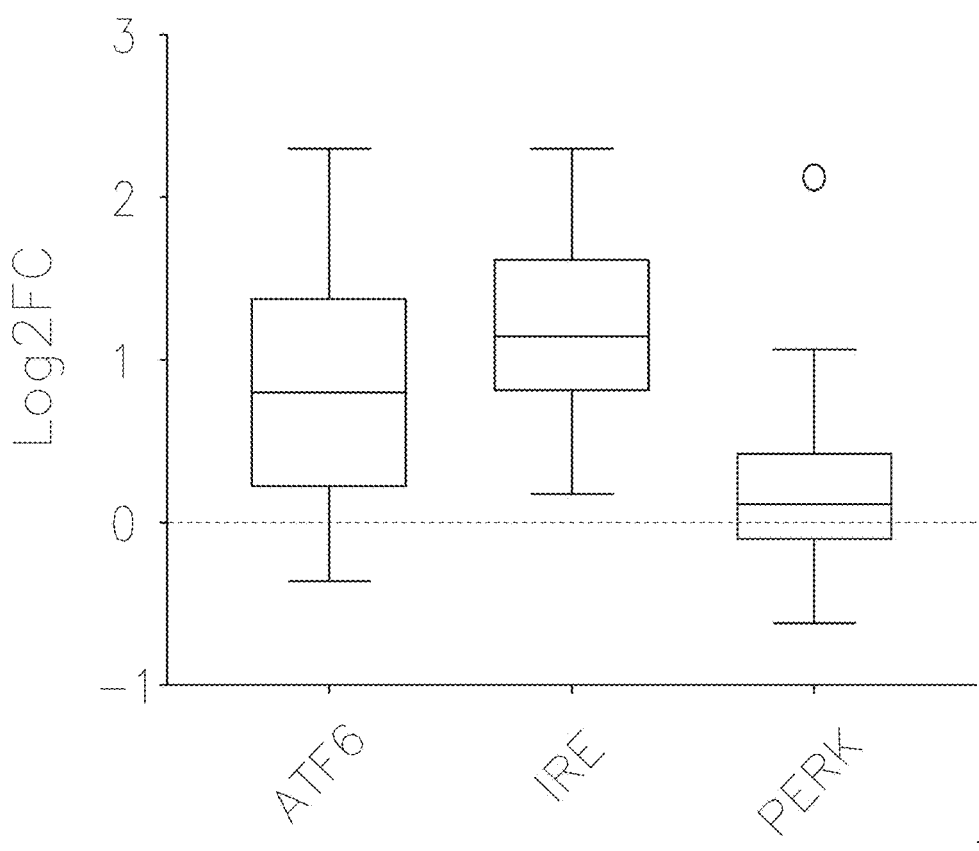
Figure 7C:
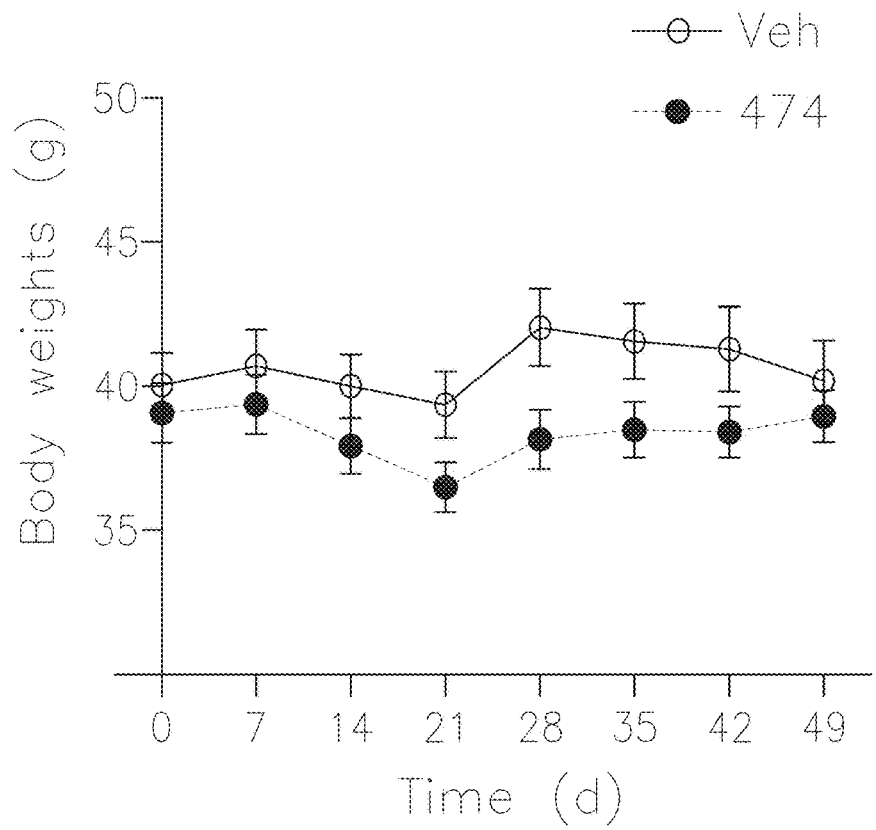
Figure 7D:
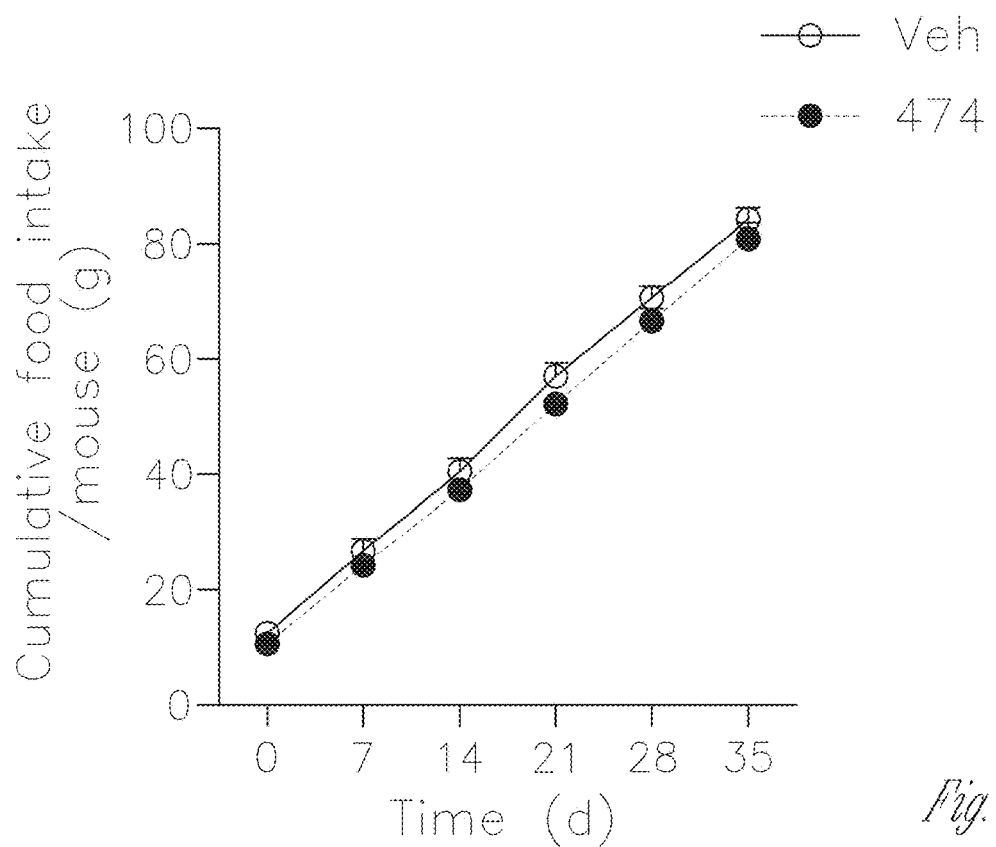

To test the efficacy of pharmacologic IRE1 activation in mitigating T2D, we chronically administered 474 by once-daily IP injections at 50 mg/kg for a period of 6 weeks to Diet-Induced Obese (DIO) mice, a model of T2D. Global RNA sequencing of livers collected from 474-treated mice revealed robust Xbp1splicing and selective activation of downstream IRE1 targets (FIG. 7B). We noted modest induction of the ATF6 transcriptional response due to the existence of a number of shared targets between the ATF6 and IRE1 arms of the UPR[8]. Notably, we saw no induction of PERK target genes, highlighting the lack of general stress response signaling (FIG. 7B), In addition, 474 treatment had no evident toxicity, with body weight and food intake remaining similar in all groups over the 6-week dosing period (FIG. 7C and FIG. 7O).

Figure 8A:
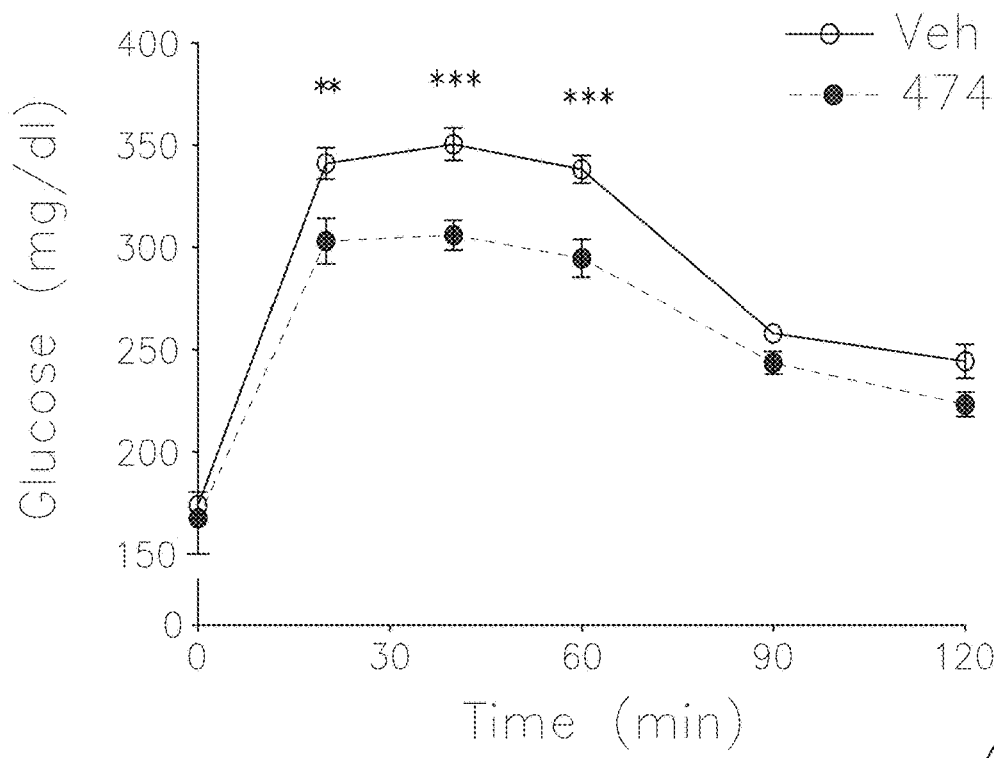
FIGS. 8A-8E. Oral glucose tolerance test in DIO mice treated with either Vehicle or 474 for 3 weeks (n=8) (FIG. 8A). Serum glucose and insulin levels post 4 weeks of dosing with 474 or vehicle (FIG. 8B). Glucose stimulated insulin secretion in islets isolated from 474 or vehicle treated mice.
Figure 8B:
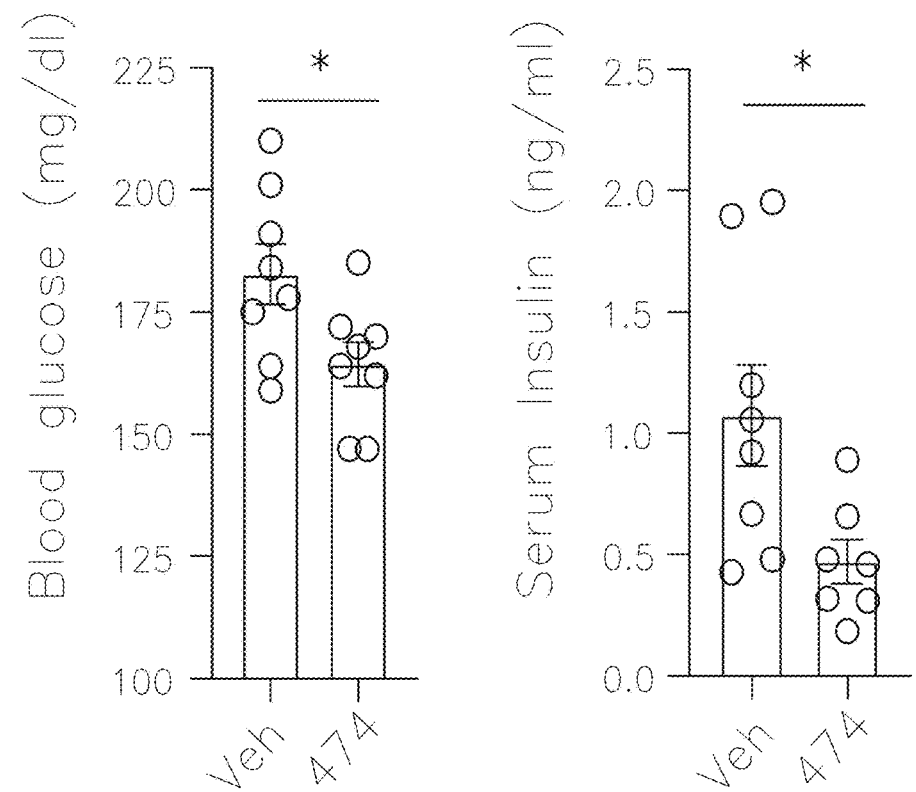
Figure 8D:
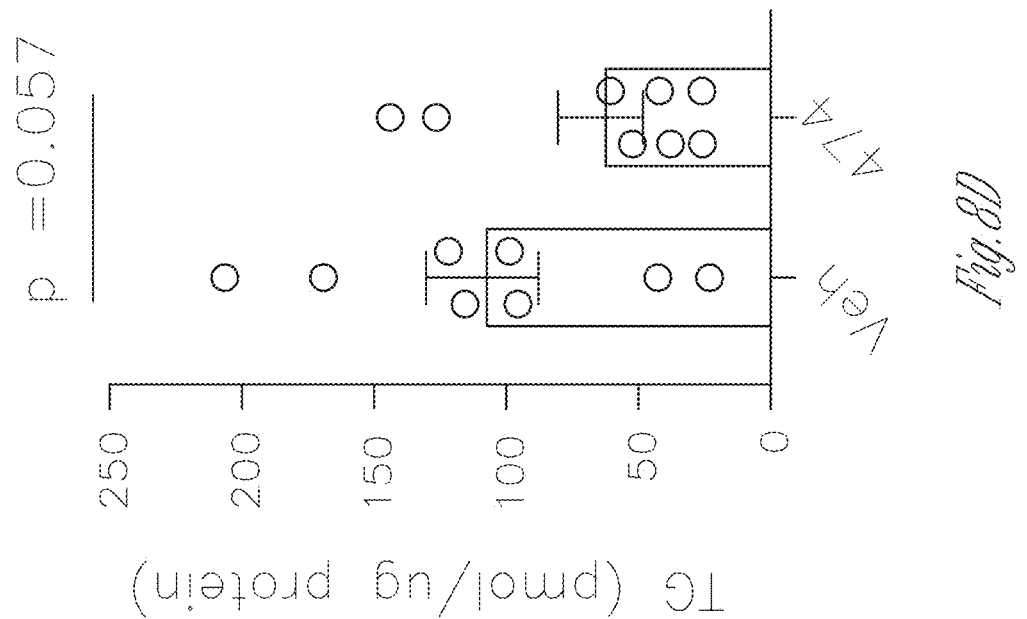
Figure 8C:
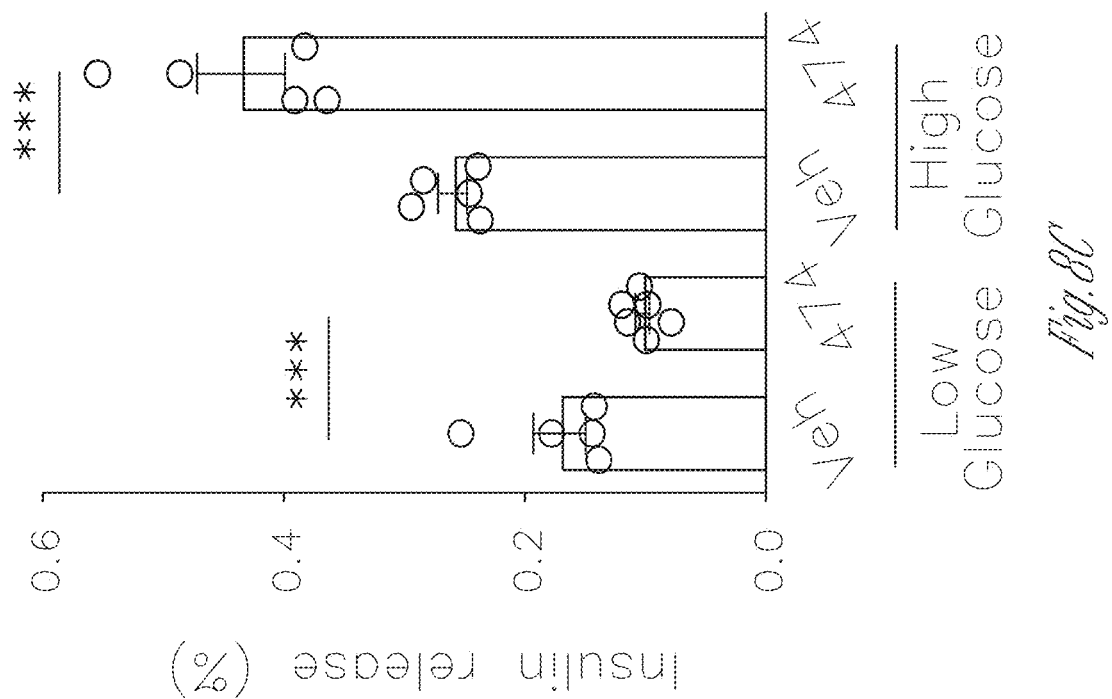
Figure 8H:
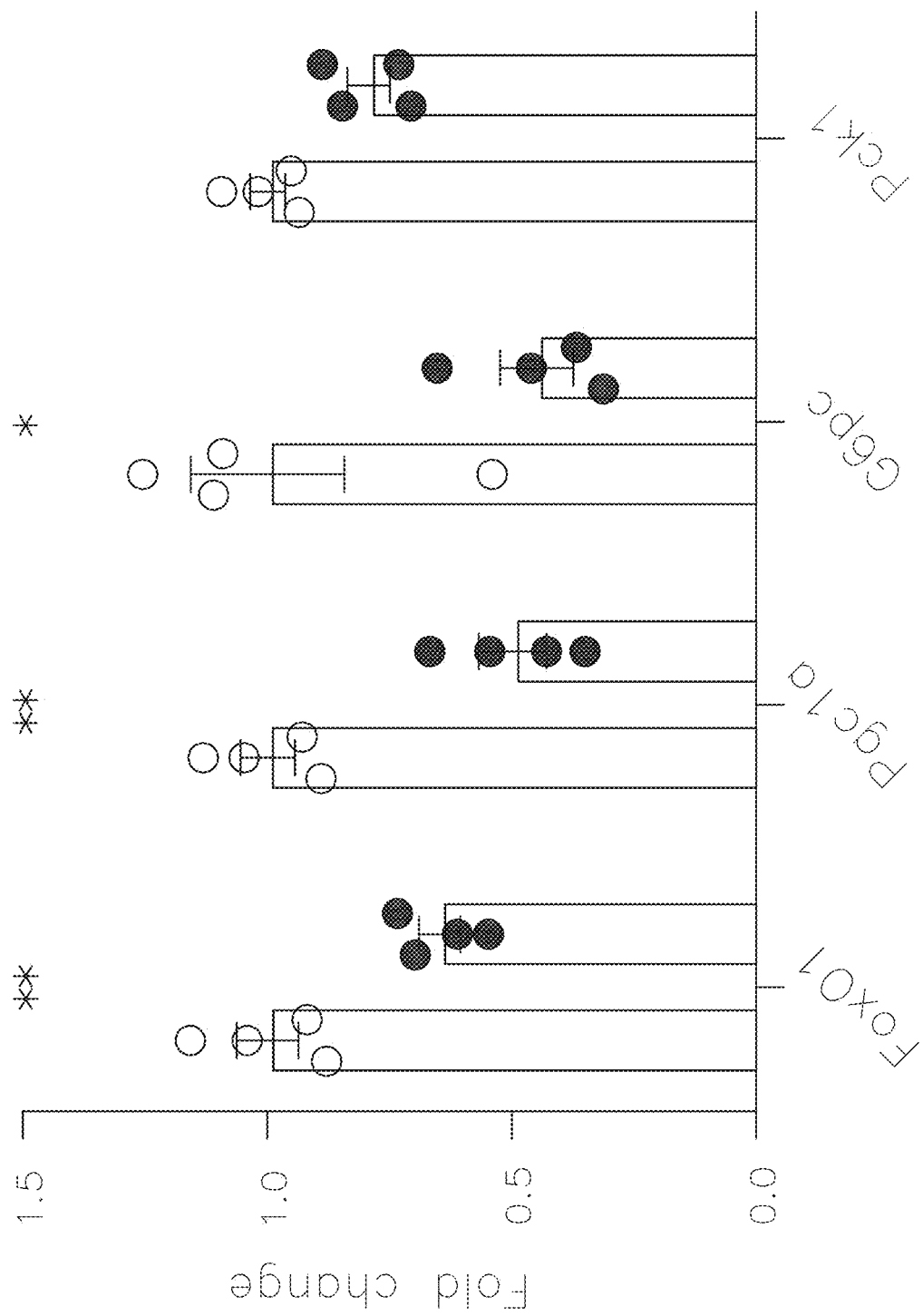

Comparison of metabolic profiles revealed significant improvements in glucose clearance in 474-treated mice as rapidly as one week into dosing, with a marked improvement observed upon continued dosing (FIG. 8A). This was accompanied by a significant reduction in fasting glucose and a more prominent decrease in basal insulin levels, evidencing improvements in systemic insulin action (FIG. 8B). This effect can be rationalized, at least in part, by enhanced pancreatic f-cell function in 474-treated DICE mice, as shown by our studies in isolated pancreatic islets from vehicle- and 474-treated mice. Upon stimulation with glucose, we noted a dramatic increase in insulin secretion from islets collected from 474-treated mice relative to vehicle-treated controls (FIG. 8C). Given the well-documented link between IRE1 and hepatic metabolism in T2D[55], we also examined markers of liver function after 474 treatment. We found reduced liver triglyceride accumulation in 474-treated mice relative to controls (FIG. 8O). Transcriptional profiling of 474-treated livers also revealed reductions in the expression of genes associated with glucose metabolism (FIG. 8E).

Additional examples illustrating embodiments of the present disclosure include the following:

Example 1 is a method for treating a disease or condition that is characterized by imbalances in proteostasis within the endoplasmic reticulum (ER) or secretory pathway, comprising administering to a subject suffering therefrom a therapeutically effective amount of a compound or a pharmaceutically acceptable salt thereof that selectively activates the inositol-requiring enzyme 1 (IRE1)/X-box binding protein 1 (XBP1s) signaling pathway of the unfolded protein response (UPR), wherein the compound does not target the IRE1 kinase domain.

Example 2 is a method for treating a disease or condition that is characterized by imbalances in proteostasis within the endoplasmic reticulum (ER) or secretory pathway, wherein the disease or condition is not associated with ER stress or activation of the unfolded protein response (UPR), the method comprising administering to a subject suffering therefrom a therapeutically effective amount of a compound or a pharmaceutically acceptable salt thereof that selectively activates the inositol-requiring enzyme 1 (IRE1)/X-box binding protein 1 (XBP1s) signaling pathway of the unfolded protein response (UPR), wherein the compound does not target the IRE1 kinase domain.

Example 3 relates to Example 1 or Example 2, wherein the disease or condition is one selected from the group consisting of diabetes, myocardial infarction, cardiovascular disease, Gaucher disease, retinal degeneration, protein misfolding, disorders, and neurodegenerative diseases.

Example 4 relates to Example 3, wherein the disease or condition is a protein misfolding disorder selected from the group consisting of amyloid diseases, Alzheimer's disease, retinal degeneration, lysosomal storage diseases, and antitrypsin associated emphysema.

Example 5 relates to Example 3 or Example 4, wherein the protein misfolding disorder is Alzheimer's disease.

Example 6 relates to Example 3, wherein the disease or condition is a neurodegenerative disease selected from the group consisting of Parkinson's disease, Huntington's disease, and peripheral nerve injury.

Example 7 relates to any one of Examples 1 to 6, wherein the compound does not substantially activate stress responsive signaling pathways other than IRE1/XBP1s.

Example 8 is a method for selectively activating the inositol-requiring enzyme 1 (IRE1)/X-box binding protein 1 (XBP1s) signaling pathway of the unfolded protein response (UPR), comprises administering to a cell a compound or a pharmaceutically acceptable salt thereof wherein the compound does not target the IRE1 kinase domain.

Example 9 relates to any one of Examples 1 to 8, wherein the compound, or a pharmaceutically acceptable salt thereof, is selected from the following table:

198
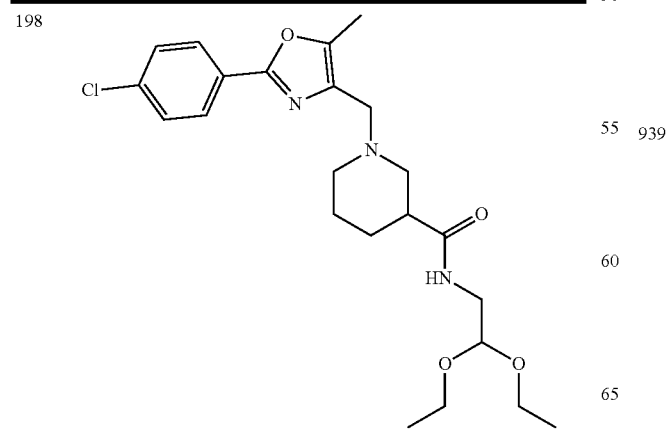

202
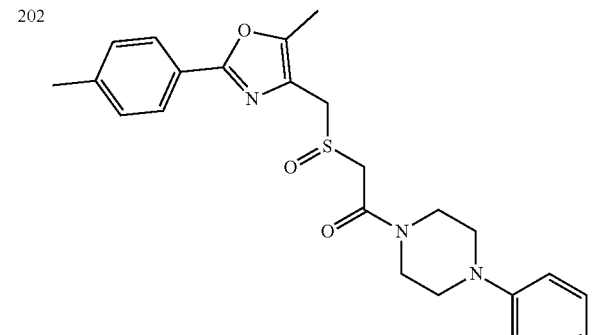

291
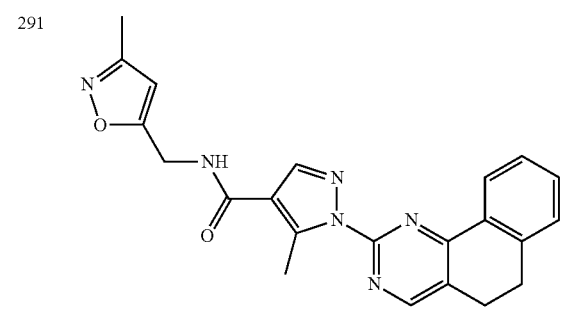

474
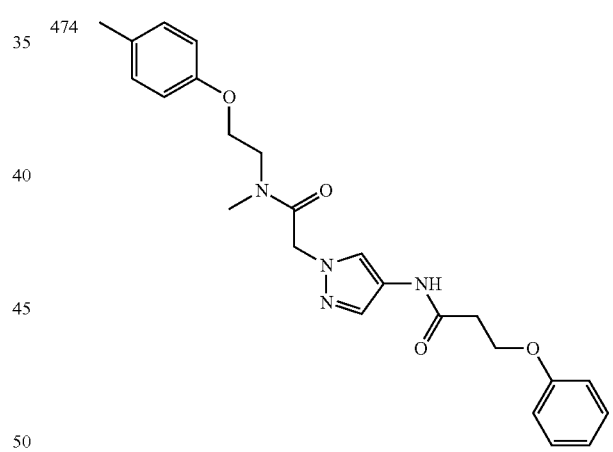

939

970

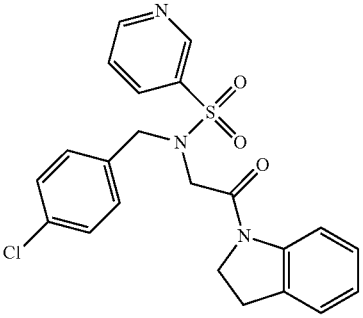 [SMILES: O=C(CN(Cc1ccc(Cl)cc1)S(=O)(=O)c1cccnc1)N1CCc2ccccc21]

967

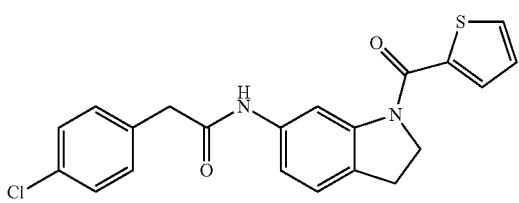 [SMILES: O=C(Cc1ccc(Cl)cc1)Nc1ccc2c(c1)N(C(=O)c1cccs1)CC2]

Example 10 relates to any one of Examples 1 to 9, wherein the compound or a pharmaceutically acceptable salt thereof is selected from the following table:

198

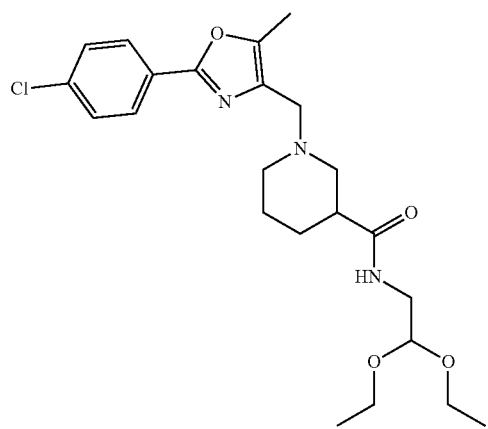 [SMILES: CCOC(CNC(=O)C1CCCN(Cc2nc(-c3ccc(Cl)cc3)oc2C)C1)OCC]

474

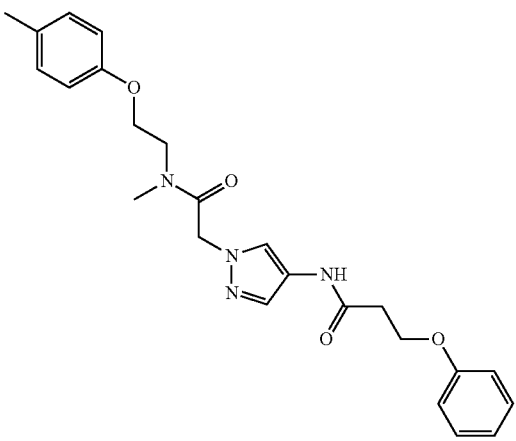 [SMILES: Cc1ccc(OCCN(C)C(=O)Cn2cc(NC(=O)CCOc3ccccc3)cn2)cc1]

970

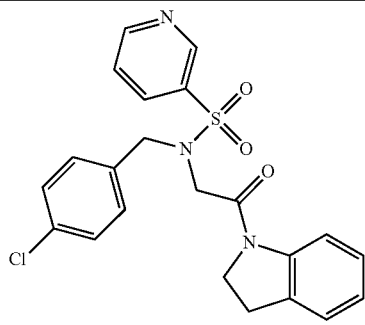

Numbered citations in the present disclosure are as follows:
1. Chakrabarti, A.; Chen, A. W.; Varner, J. D., A review of the mammalian unfolded protein response. *Biotechnol Bioeng* 2011, 108 (12), 2777-93.
2. Walter, P.; Ron, D., The unfolded protein response: from stress pathway to homeostatic regulation. *Science* 2011, 334 (6059), 1081-6.
3. Bernales, S.; Papa, F. R.; Walter, P., Intracellular signaling by the unfolded protein response. *Annu Rev Cell Dev Biol* 2006, 22, 487-508.
4. Schroder, M.; Kaufman, R. J., ER stress and the unfolded protein response. *Mutat Res* 2005, 569 (1-2), 29-63.
5. Zhang, K.; Kaufman, R. J., Signaling the unfolded protein response from the endoplasmic reticulum. *J Biol Chem* 2004, 279 (25), 25935-8.
6. Patil, C.; Walter, P., Intracellular signaling from the endoplasmic reticulum to the nucleus: the unfolded protein response in yeast and mammals. *Curr Opin Cell Biol* 2001, 13 (3), 349-55.
7. Ron, D., Translational control in the endoplasmic reticulum stress response. *J Clin Invest* 2002, 110 (10), 1383-8.
8. Shoulders, M. D.; Ryno, L. M.; Genereux, J. C.; Moresco, J. J.; Tu, P. G.; Wu, C.; Yates, J. R., 3rd; Su, A. Kelly, J. W.; Wiseman, R. L., Stress-independent activation of XBP1s and/or ATF6 reveals three functionally diverse ER proteostasis environments. *Cell Rep* 2013, 3 (4), 1279-92,
9. Lebeau, J., Saunders, J. M.; Moraes, V. W. R.; Madhavan, A.; Madrazo, N.; Anthony, M. C.; Wiseman, R. L., The PERK Arm of the Unfolded Protein Response Regulates Mitochondrial Morphology during Acute Endoplasmic Reticulum Stress. *Cell Rep* 2018, 22 (11), 2827-2836.
10. Lee, A. H.; Iwakoshi, N. N.; Glimcher, L. H., XBP-1 regulates a subset of endoplasmic reticulum resident chaperone genes in the unfolded protein response. *Mol Cell Biol* 2003, 23 (21), 7448-59.
11, Han, J.; Back, S. H.; Hur, J.; Lin, Y. H.; Gildersleeve, R.; Shan, J.; Yuan, C. L.; Krokowski, D.; Wang, S.; Hatzoglou, M.; Kilberg M. S.; Sartor, M. A.; Kaufman, R. J., ER-stress-induced transcriptional regulation increases protein synthesis leading to cell death. *Nat Cell Biol* 2013, 15 (5), 481-90.
12. Chang, T. K.; Lawrence, D. A.; Lu, M.; Tan, J.; Harnoss, J. M.; Marsters, S. A.; Liu, P.; Sandoval, W.; Martin, S. E.; Ashkenazi, A., Coordination between Two Branches of the Unfolded Protein Response Determines Apoptotic Cell Fate. *Mol Cell* 2018, 71 (4), 629-636 e5.

13. Balch, W. E.; Morimoto, R. I.; Dillin, A.; Kelly, J. W., Adapting proteostasis for disease intervention. *Science* 2008, 319 (5865), 916-9.
14. Chen, J. J.; Genereux, J. C.; Wiseman, R. L., Endoplasmic reticulum quality control and systemic amyloid disease: Impacting protein stability from the inside out. *IUBMB Life* 2015, 67 (6), 404-13.
15. Wong, M. Y.; Shoulders, M. Targeting defective proteostasis in the collagenopathies. *Curr Opin Chem Biol* 2019, 50, 80-88.
16. Zhang, Zhang, C.; Wang, A., Divergence and Conservation of the Major UPR Branch IRE1-bZIP Signaling Pathway across Eukaryotes. *Sci Rep* 2016, 6, 27362.
17. Joshi, A.; Newbatt, Y.; McAndrew, P. C.; Stubbs, M.; Burke, R.; Richards, M. W.; Bhatia, C.; Caldwell, J. J.; McHardy, T.; Collins, I.; Bayliss, R., Molecular mechanisms of human IRE1 activation through dimerization and ligand binding. *Oncotarget* 2015, 6 (15), 13019-35.
18. Korennykh, A. V.; Egea, P. F.; Korostelev, A. A.; Finer-Moore, J.; Zhang, C.; Shokat, K. M.; Stroud, R. M.; Walter, P., The unfolded protein response signals through high-order assembly of Ire1. *Nature* 2009, 457 (7230), 687-93.
19. Ali, M. M.; Bagratuni, T.; Davenport, E. L.; Nowak, P. R.; Silva-Santisteban, M. C.; Hardcastle, A.; McAndrews, C.; Rowlands, M. G.; Morgan, G. J.; Aherne, W.; Collins, I.; Davies, F. E.; Pearl, L. H., Structure of the IRE1 autophosphorylation complex and implications for the unfolded protein response. *EMBO J* 2011, 30 (5), 894-905.
20. Wang, L.; Perera, B. G.; Hari, S. B.; Bhhatarai, B.; Backes, B. J.; Seeliger, M. A.; Schurer, S. C.; Oakes, S. A.; Papa, F. R.; Maly, D. J., Divergent allosteric control of the IRE1 alpha endoribonuclease using kinase inhibitors. *Nat Chem Biol* 2012, 8 (12), 982-9.
21. Yoshida, H.; Matsui, T.; Yamamoto, A.; Okada, T.; Mori, K., XBP1 mRNA is induced by ATF6 and spliced by IRE1 in response to ER stress to produce a highly active transcription factor. *Cell* 2001, 107 (7), 881-91.
22. Hollien, J.; Lin, J. H.; Li, H.; Stevens, N.; Walter, P.; Weissman, J. S., Regulated Ire1-dependent decay of messenger RNAs in mammalian cells. *J Cell Biol* 2009, 186 (3), 323-31.
23. Tam, A. B.; Koong, A. C.; Niwa, M., Ire1 has distinct catalytic mechanisms for XBP1/HAC1 splicing and RIDD. *Cell Rep* 2014, 9 (3), 850-8.
24. Bae, D.; Moore, K. A.; Mella, J. M.; Hayashi, S. Y.; Hollien, J., Degradation of Blos1 mRNA by IRE1 repositions lysosomes and protects cells from stress. *J Cell Biol* 2019, 218 (4), 1118-4127.
25. Lin, J. H.; Li, H.; Yasumura, D.; Cohen, H. R.; Zhang, C.; Panning, B.; Shokat, K. M.; Lavail, M. M.; Walter, P., IRE1 signaling affects cell fate during the unfolded protein response. *Science* 2007, 318 (5852), 944-9.
26. Valdes, P.; Mercado, G.; Vidal, R. L.; Molina, C.; Parsons, G.; Court, F. A.; Martinez, A.; Galleguillos, D.; Armentano, D.; Schneider, B. L.; Hetz, C., Control of dopaminergic neuron survival by the unfolded protein response transcription factor XBP1. *Proc Natl Acad Sci USA* 2014, 111 (18), 6804-9.
27. Zuleta, A.; Vidal, R. L.; Armentano, D.; Parsons, G.; Hetz, C., AAV-mediated delivery of the transcription factor XBP1s into the striatum reduces mutant Huntingtin aggregation in a mouse model of Huntington's disease. *Biochem Biophys Res Commun* 2012, 420 (3), 558-63.
28. Valenzuela, V.; Collyer, E.; Armentano, D.; Parsons, G. B.; Court, F. A.; Hetz, C., Activation of the unfolded protein response enhances motor recovery after spinal cord injury. *Cell Death Dis* 2012, 3, 0272
29. Chiang, W. C.; Messah, C.; Lin. J. H., IRE1 directs proteasomal and lysosomal degradation of misfolded rhodopsin. *Mol Biol Cell* 2012, 23 (5), 758-70.
30. Sifers, R. N., intracellular processing of alpha1-antitrypsin. *Proc Am Thorac Soc* 2010, 7 (6), 376-80.
31, Cui, H.; Deng, M.; Zhang, Y.; Yin, F.; Liu, J., Genipiside Increases Unfolded Protein Response-Mediating HRD1 Expression to Accelerate APP Degradation in Primary Cortical Neurons. *Neurochem Res* 2018, 43 (3), 669-680.
32. Kaneko, M.; Koike, H.; Saito, R.; Kitamura, Y.; Okuma, Y.; Nomura, Y., Loss of HRD1-mediated protein degradation causes amyloid precursor protein accumulation and amyloid-beta generation. *J Neurosci* 2010, 30 (11), 3924-32.
33, Ozcan, U.; Cao, Q.; Yilmaz, E.; Lee, A. H.; Iwakoshi, N. N.; Ozdelen, E.; Tuncman, G.; Gorgun, C.; Glimcher, L. H.; Hotamisligil, G. S., Endoplasmic reticulum stress links obesity, insulin action, and type 2 diabetes. *Science* 2004, 306 (5695), 457-61.
34. Bi, X.; Zhang, G.; Wang, X.; Nguyen, C.; May, H. I.; Li, X.; Al-Hashimi, A. A.; Austin, R. C.; Gillette, T. G.; Fu, G.; Wang, Z. V.; Hill, J. A., Endoplasmic Reticulum Chaperone GRP78 Protects Heart From Ischemia/ Reperfusion Injury Through Akt Activation. *Circ Res* 2018, 122 (11), 1545-1554.
35. Mendez, A. S.; Alfaro, Morales-Soto, M. A.; Dar, A. C.; McCullagh, E.; Gotthardt, K.; Li, H.; Acosta-Alvear, D.; Sidrauski, C.; Korennykh, A. V.; Bernales, S.; Shokat, K. M.; Walter, P., Endoplasmic reticulum stress-independent activation of unfolded protein response kinases by a small molecule ATP-mimic. *Elife* 2015, 4.
36. Ghosh, R.; Wang, L.; Wang, E. S.; Perera, B. G.; Igbaria, A.; Morita, S.; Prado, K.; Thamsen, M.; Caswell, D.; Macias, H.; Weiberth, K. F.; Gliedt, M. J.; Alavi, M. V.; Hari, S. B.; Mitra, A. K.; Bhhatarai, B.; Schurer, S. C.; Snapp, E. L.; Gould, D. B.; German, M. S.; Backes, B. J.; Maly, D. J.; Oakes, S. A.; Papa, F. R., Allosteric inhibition of the IRE1 alpha RNase preserves cell viability and function during endoplasmic reticulum stress. *Cell* 2014, 158 (3), 534-48.
37. Plate, L.; Cooley, C. B.; Chen, J. J.; Paxman, R. J.; Gallagher, C. M.; Madoux, F.; Genereux, J. C.; Dobbs, W.; Garza, D.; Spicer, T. P.; Scampavia, L.; Brown, S. J.; Rosen, H.; Powers, E. T.; Walter, P.; Hodder, P.; Wiseman, R. L.; Kelly, J. W., Small molecule proteostasis regulators that reprogram the ER to reduce extracellular protein aggregation. *Elife* 2016, 5.
38. Calamini, B.; Silva, M. C.; Madoux, F.; Hutt, D. M.; Khanna, S.; Chalfant, M. A.; Saldanha., S. A.; Hodder, P.; Tait, B. D.; Garza, D.; Balch, W. E.; Morimoto, R. Small-molecule proteostasis regulators for protein conformational diseases. *Nat Chem Biol* 2011, 8 (2), 185-96.
39. Merour, J. Y.; Buron, F.; Pie, K.; Bonnet, P.; Routier, S., The azaindole framework in the design of kinase inhibitors. *Molecules* 2014, 19 (12), 19935-79.
40. Lu, P. D.; Jousse, C.; Marciniak, S. J.; Zhang, Y.; Novoa, I.; Scheuner, D.; Kaufman, R. J.; Ron, D.; Harding, H. P., Cytoprotection by pre-emptive conditional phosphorylation of translation initiation factor 2. *EMBO J* 2004, 23 (1), 169-79.

41. Xue, He, Y.; Ye, K.; Gu, Z.; Mao, Y.; Qi, L., A conserved structural determinant located at the interdomain region of mammalian inositol-requiring enzyme 1 alpha. *J Biol Chem* 2011, 286 (35), 30859-66.
42. Grandjean, J. M. D.; Plate, L.; Morimoto, R. I.; Bollong, M. J.; Powers, E. T.; Wiseman, R. L., Deconvoluting Stress-Responsive Proteostasis Signaling Pathways for Pharmacologic Activation Using Targeted RNA Sequencing. *ACS Chem Biol* 2019, 14 (4), 784-795.
43. Moore, K.; Hollien, J., Ire1-mediated decay in mammalian cells relies on mRNA sequence, structure, and translational status. *Mol Biol Cell* 2015, 26 (16), 2873-84.
44. Chow, V. W.; Mattson, M. P.; Wong, P. C.; Gleichmann, M., An overview of APP processing enzymes and products. *Neuromolecular Med* 2010, 12 (1), 1-12.
45. Portelius, E.; Olsson, M.; Brinkmalm, G.; Ruetschi, U.; Mattsson, N.; Andreasson, U.; Gobom, J.; Brinkmalm, A.; Holtta, M.; Blennow, K.; Zetterberg, H., Mass spectrometric characterization of amyloid-beta species in the 7PA2 cell model of Alzheimer's disease. *J Alzheimers Dis* 2013, 33 (1), 85-93.
46. Pera, M.; Larrea, D.; Guardia-Laguarta, C.; Montesinos, J.; Velasco, K. R.; Agrawal, R. R.; Xu, Y.; Chan, R. B.; Di Paolo, G.; Mehler, M. F.; Perumal, G. S.; Macaluso, F. P.; Freyberg, Z. Z.; Acin-Perez, R.; Enriquez, J. A.; Schon, E. A.; Area-Gomez, E., Increased localization of APP-C99 in mitochondria-associated ER membranes causes mitochondrial dysfunction in Alzheimer disease. *EMBO J* 2017, 36 (22), 3356-3371.
47. Krako, N.; Magnifico, M. C.; Arese, M.; Meli, G.; Forte, E.; Lecci, A.; Manca, A.; Giuffre, A.; Mastronicola, D.; Sarti, P.; Cattaneo, A., Characterization of mitochondrial dysfunction in the 7PA2 cell model of Alzheimer's disease. *J Alzheimers Dis* 2013, 37 (4), 747-58.
48. Rainbolt, T. K.; Lebeau, J.; Puchades, C.; Wiseman, R. L., Reciprocal Degradation of YME1L and OMA1 Adapts Mitochondrial Proteolytic Activity during Stress. *Cell Rep* 2016, 14 (9), 2041-2049.
49. Blackwood, E. A.; Azizi, K.; Thuerauf, D. J.; Paxman, R. J.; Plate, L.; Kelly, J. W.; Wiseman, R Glembotski, C. C., Pharmacologic ATF6 activation confers global protection in widespread disease models by reprograming cellular proteostasis. *Nat Commun* 2019, 10 (1), 187.
50. Kroeger, H.; Grimsey, N.; Paxman, R.; Chiang, W. C.; Plate, L.; Jones, Y.; Shaw, P. X.; Trejo, J.; Tsang, S. H.; Powers, E.; Kelly, J. W.; Wiseman, R. L.; J. H., The unfolded protein response regulator ATF6 promotes mesodermal differentiation. *Sci Signal* 2018, 11 (517).
51. Casas-Tinto, S.; Zhang, Y.; Sanchez-Garcia, J.; Gomez-Velazquez, M.; Rincon-Limas, D. E.; Fernandez-Funez, P., The ER stress factor XBP1s prevents amyloid-beta neurotoxicity. *Hum Mol Genet* 2011, 20 (11), 2144-60.
52. Tufanli, O.; Telkoparan Akillilar, P.; Acosta-Alvear, D.; Kocaturk, B.; Onat, U. I.; Hamid, S. M.; Cimen, I.; Walter, P.; Weber, C.; Erbay, E., Targeting IRE1 with small molecules counteracts progression of atherosclerosis. *Proc Acad Sci USA* 2017, 114 (8), E1395-E1404.
53. Rosen, D. A.; Seki, S. M.; Fernandez-Castaneda, A.; Reiter, R. M.; Eccles, J. D.; Woodfolk, J. A.; Gaultier, A., Modulation of the sigma-1 receptor-IRE1 pathway is beneficial in preclinical models of inflammation and sepsis. *Sci Transl Med* 2019, 11 (478).
54. Wang, S.; Kaufman, R. J., The impact of the unfolded protein response on human disease. *J Cell Biol* 2012, 197 (7), 857-67.
55. Zhou, Y. et al. Regulation of glucose homeostasis through a XBP-1-FoxO1 interaction. *Nat Med* 17, 356-365, doi:10.1038/nm.2293 (2011).
56. O'Rahilly, S. et al. The IRE1α/XBP1s Pathway Is Essential for the Glucose Response and Protection of β Cells. *PLOS Biology* 13, doi:10.1371/journal.pbio.1002277 (2015).

We claim:

1. A method for treating a disease or condition that is characterized by imbalances in proteostasis within the endoplasmic reticulum (ER) or secretory pathway, comprising administering to a subject suffering therefrom a therapeutically effective amount of a compound or a pharmaceutically acceptable salt thereof that selectively activates the inositol-requiring enzyme 1 (IRE1)/X-box binding protein 1 (XBP1s) signaling pathway of the unfolded protein response (UPR) independent of other UPR signaling pathways, wherein the compound does not inhibit IRE1 kinase activity.

2. The method of claim 1, wherein the compound activates the inositol-requiring enzyme 1 (IRE1)/X-box binding protein 1 (XBP1s) signaling pathway of the unfolded protein response (UPR) at a level 1.5-2.0 times higher than ATF6 transcriptional signaling.

3. The method according to claim 1, wherein the disease or condition is one selected from the group consisting of diabetes, myocardial infarction, cardiovascular disease, Gaucher disease, retinal degeneration, protein misfolding disorders, and neurodegenerative diseases.

4. The method according to claim 3, wherein the disease or condition is a neurodegenerative disease selected from the group consisting of Parkinson's disease, Huntington's disease, and peripheral nerve injury.

5. The method according to claim 3, wherein the disease or condition is a protein misfolding disorder selected from the group consisting of amyloid diseases, Alzheimer's disease, retinal degeneration, lysosomal storage diseases, and antitrypsin associated emphysema.

6. The method according to claim 5, wherein the protein misfolding disorder is Alzheimer's disease.

7. The method according to claim 1, wherein the compound is selected from the following table:

198

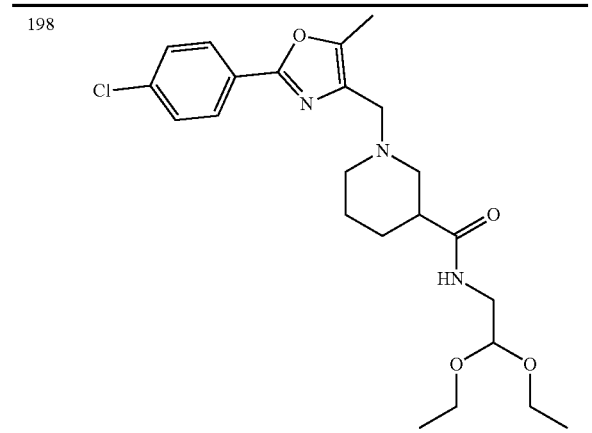

| | |
|---|---|
| 202 | 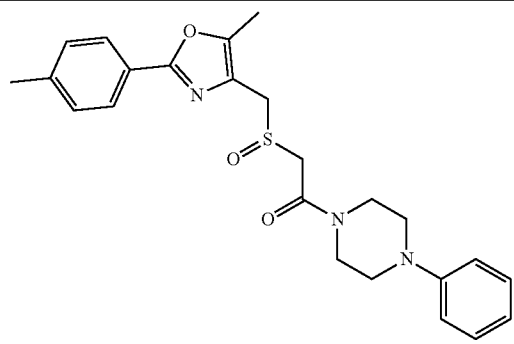 |
| 291 | 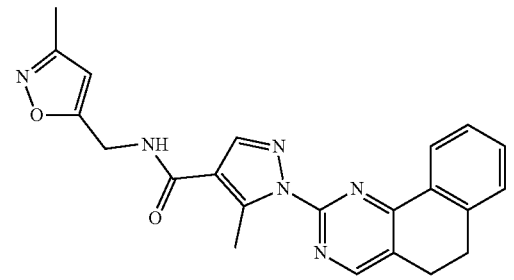 [SMILES: Cc1cc(CNC(=O)c2cnn(-c3ncc4c(n3)-c3ccccc3CC4)c2C)on1] |
| 474 | 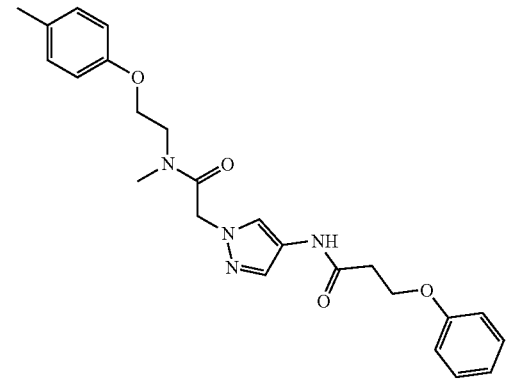 [SMILES: Cc1ccc(OCCN(C)C(=O)Cn2cc(NC(=O)CCOc3ccccc3)cn2)cc1] |
| 939 | 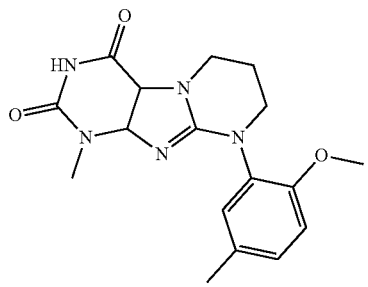 [SMILES: COc1ccc(C)cc1N1CCCN2C1=NC1C2C(=O)NC(=O)N1C] |
| 970 | 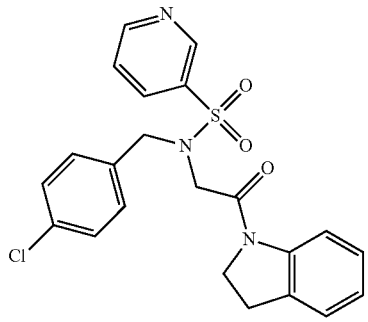 [SMILES: O=C(CN(Cc1ccc(Cl)cc1)S(=O)(=O)c1cccnc1)N1CCc2ccccc21] |
| | |
|---|---|
| 967 | 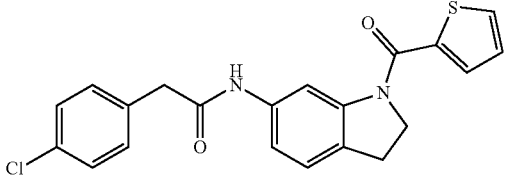 [SMILES: O=C(Cc1ccc(Cl)cc1)Nc1ccc2c(c1)N(C(=O)c1cccs1)CC2] |
and pharmaceutically acceptable salts thereof.
8. The method according to claim 7, wherein the compound is selected from the following table:
| | |
|---|---|
| 198 | 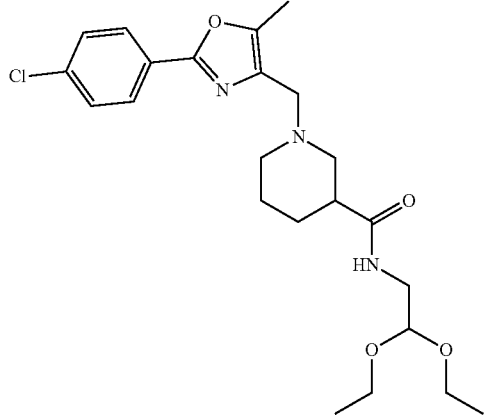 [SMILES: CCOC(CNC(=O)C1CCCN(Cc2nc(-c3ccc(Cl)cc3)oc2C)C1)OCC] |
| 474 | 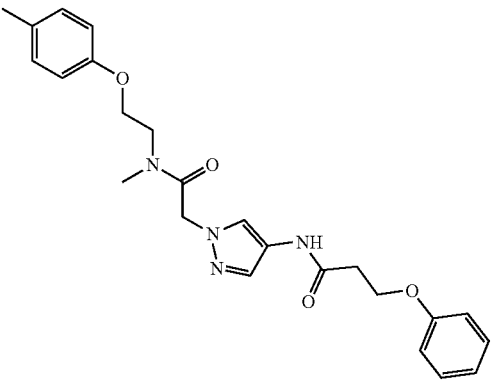 [SMILES: Cc1ccc(OCCN(C)C(=O)Cn2cc(NC(=O)CCOc3ccccc3)cn2)cc1] |
| 970 | 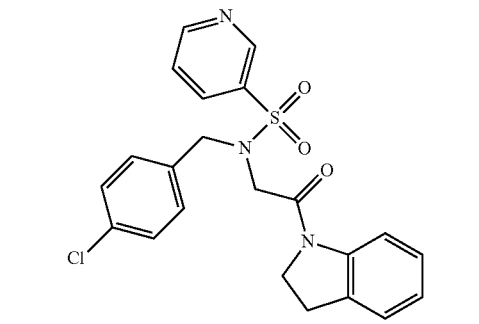 [SMILES: O=C(CN(Cc1ccc(Cl)cc1)S(=O)(=O)c1cccnc1)N1CCc2ccccc21] |
and pharmaceutically acceptable salts thereof.
9. The method according to claim 3, wherein the compound is selected from the following table:

198 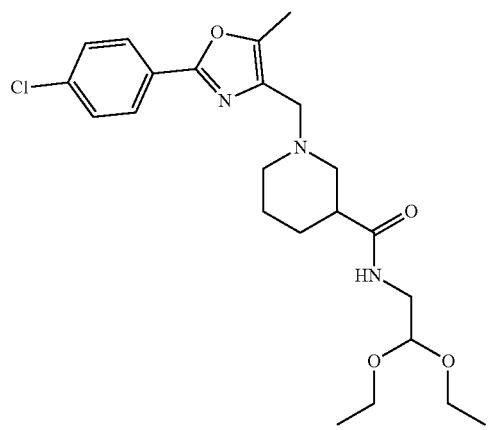 [SMILES: CCOC(CNC(=O)C1CCCN(Cc2nc(-c3ccc(Cl)cc3)oc2C)C1)OCC]
939 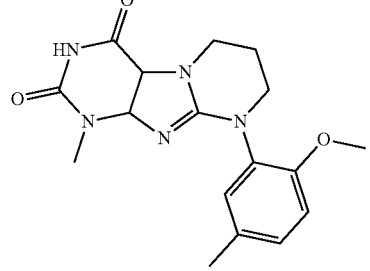
202 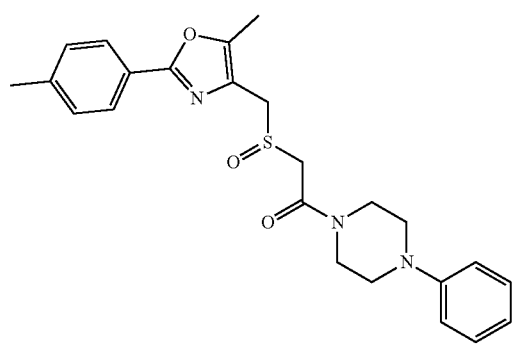 [SMILES: Cc1ccc(-c2nc(CS(=O)CC(=O)N3CCN(c4ccccc4)CC3)c(C)o2)cc1]
967 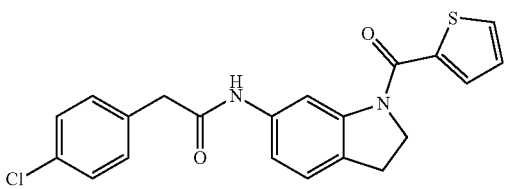
291 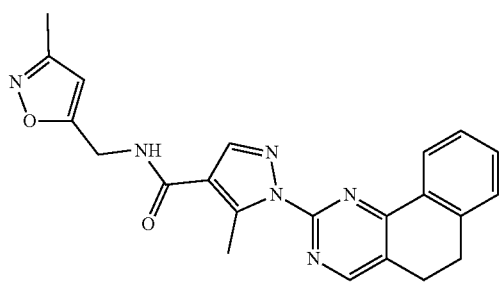 [SMILES: Cc1cc(CNC(=O)c2cnn(-c3ncc4c(n3)-c3ccccc3CC4)c2C)on1]
970 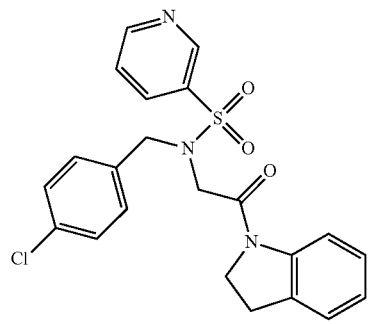 [SMILES: O=C(CN(Cc1ccc(Cl)cc1)S(=O)(=O)c1cccnc1)N1CCc2ccccc21]
474 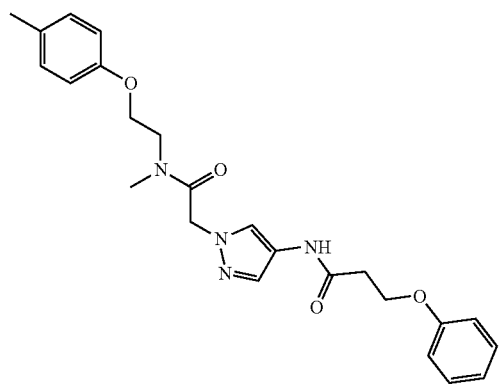 [SMILES: Cc1ccc(OCCN(C)C(=O)Cn2cc(NC(=O)CCOc3ccccc3)cn2)cc1]
and pharmaceutically acceptable salts thereof.
10. The method according to claim 9, wherein the compound is selected from the following table:
198 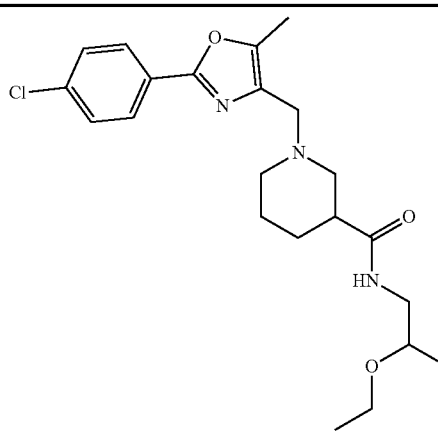

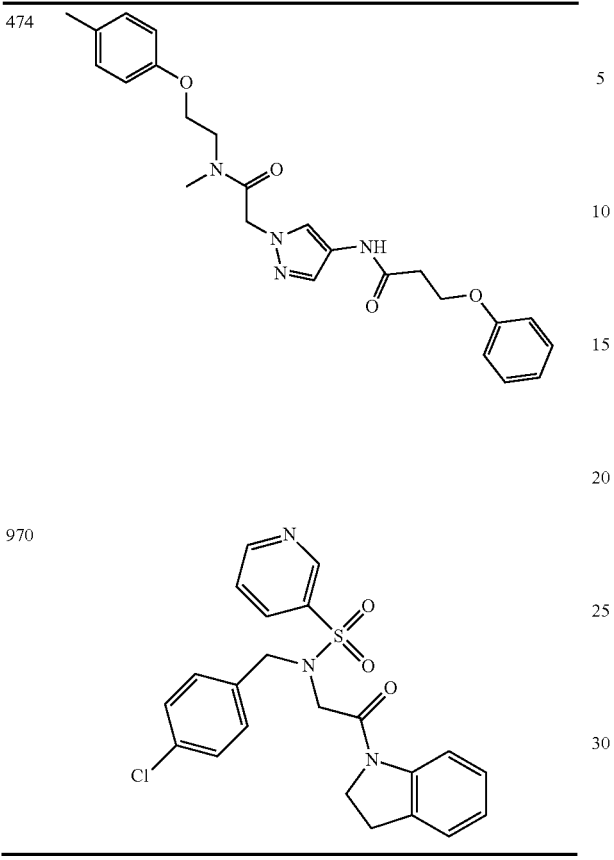

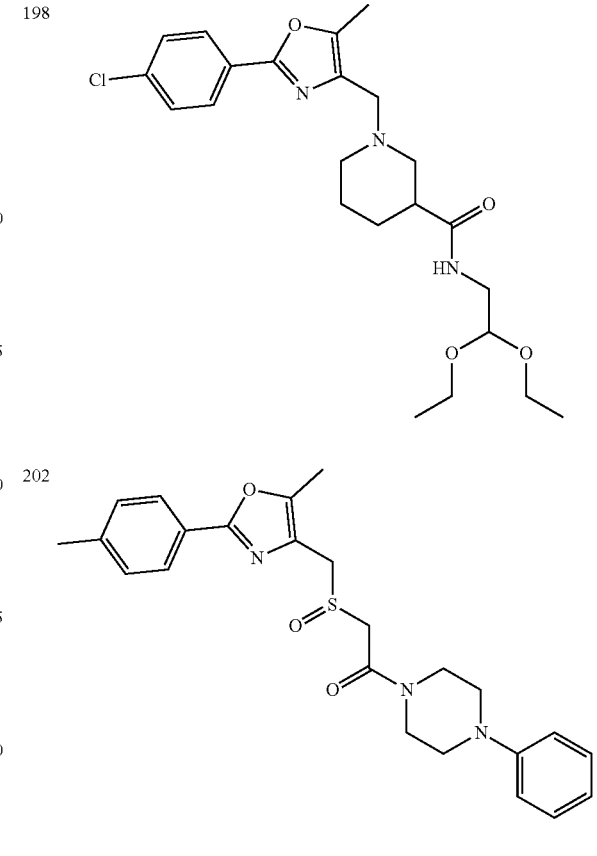

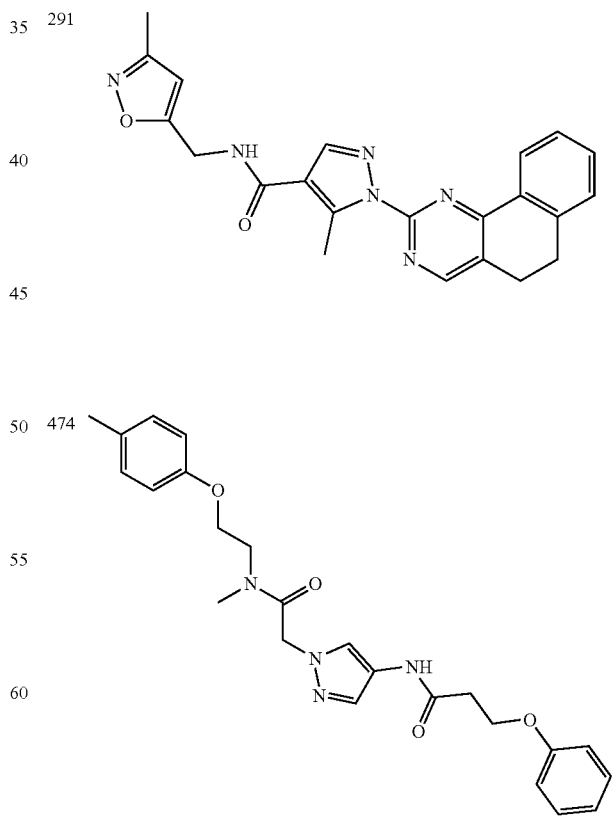

and pharmaceutically acceptable salts thereof.

11. A method for treating a disease or condition that is characterized by imbalances in proteostasis within the endoplasmic reticulum (ER) or secretory pathway, wherein the disease or condition is not associated with activation of the inositol-requiring enzyme 1 (IRE1)/X-box binding protein 1 (XBP1s) signaling pathway of the unfolded protein response (UPR), the method comprising administering to a subject suffering therefrom a therapeutically effective amount of a compound or a pharmaceutically acceptable salt thereof that selectively activates the inositol-requiring enzyme 1 (IRE1)/X-box binding protein 1 (XBP1s) signaling pathway of the unfolded protein response (UPR) independent of other UPR signaling pathways, wherein the compound does not inhibit IRE1 kinase activity.

12. The method according to claim 11, wherein the disease or condition is one selected from the group consisting of diabetes, myocardial infarction, cardiovascular disease, Gaucher disease, retinal degeneration, protein misfolding disorders, and neurodegenerative diseases.

13. The method according to claim 12, wherein the disease or condition is a protein misfolding disorder selected from the group consisting of amyloid diseases, Alzheimer's disease, retinal degeneration, lysosomal storage diseases, and antitrypsin associated emphysema.

14. The method according to claim 13, wherein the protein misfolding disorder is Alzheimer's disease.

15. The method according to claim 11, wherein the compound is selected from the following table:

939 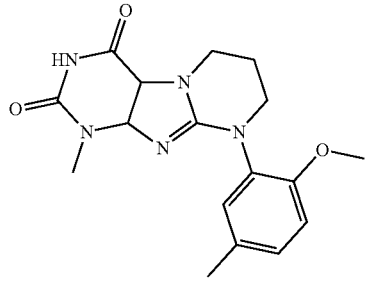 [SMILES: COc1ccc(C)cc1N1CCCN2C1=NC1C2C(=O)NC(=O)N1C]
970 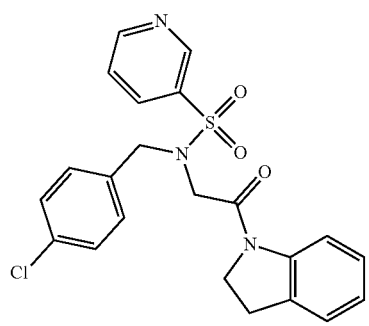 [SMILES: O=C(CN(Cc1ccc(Cl)cc1)S(=O)(=O)c1cccnc1)N1CCc2ccccc21]
967 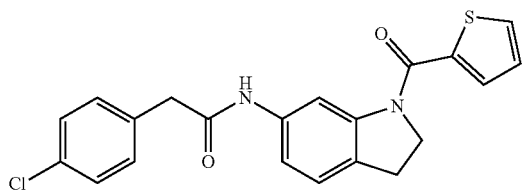 [SMILES: O=C(Cc1ccc(Cl)cc1)Nc1ccc2c(c1)N(C(=O)c1cccs1)CC2]
and pharmaceutically acceptable salts thereof.
16. The method according to claim 15, wherein the compound is selected from the following table:
198 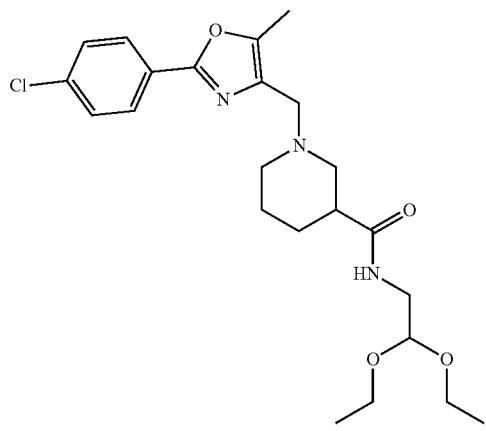 [SMILES: CCOC(CNC(=O)C1CCCN(Cc2nc(-c3ccc(Cl)cc3)oc2C)C1)OCC]
474 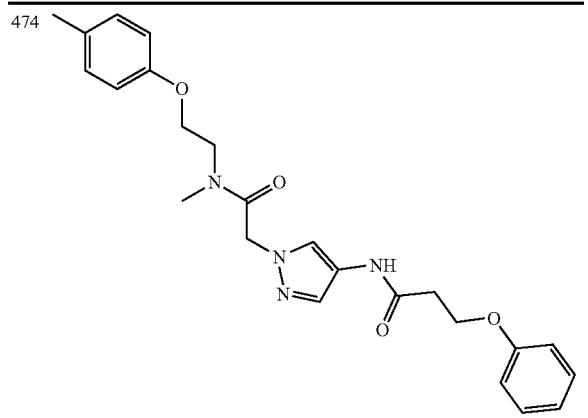
970 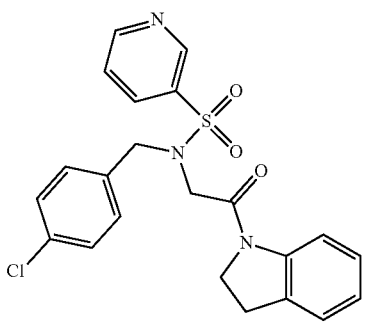 [SMILES: O=C(CN(Cc1ccc(Cl)cc1)S(=O)(=O)c1cccnc1)N1CCc2ccccc21]
and pharmaceutically acceptable salts thereof.
17. The method according to claim 12, wherein the compound is selected from the following table:
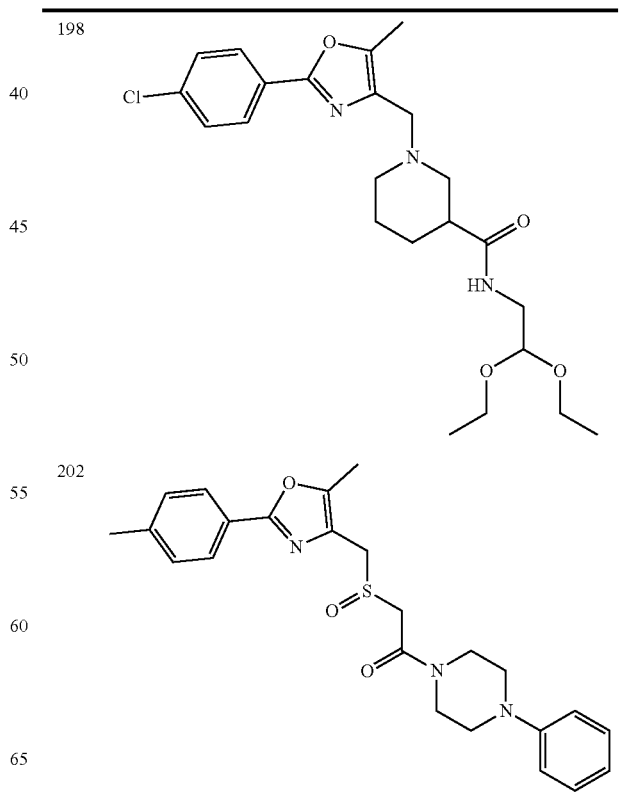

291 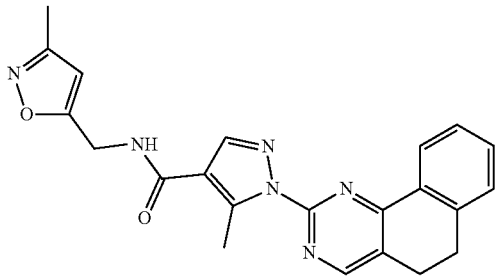 [SMILES: Cc1cc(CNC(=O)c2cnn(-c3ncc4c(n3)-c3ccccc3CC4)c2C)on1]

474 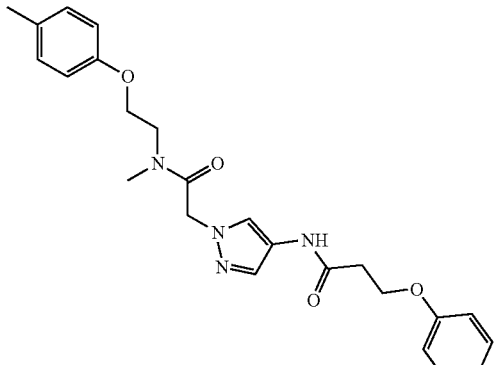

939 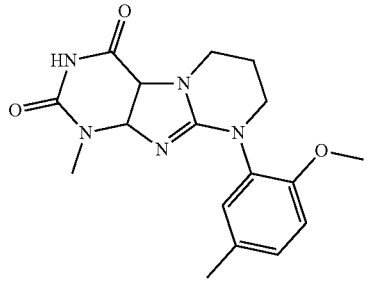 [SMILES: COc1ccc(C)cc1N1CCCN2C1=NC1C2C(=O)NC(=O)N1C]

967 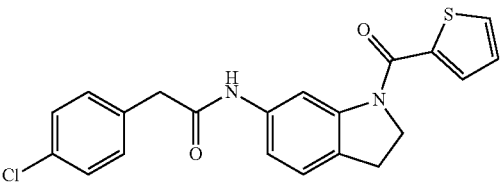 [SMILES: O=C(Cc1ccc(Cl)cc1)Nc1ccc2c(c1)N(C(=O)c1cccs1)CC2]

970 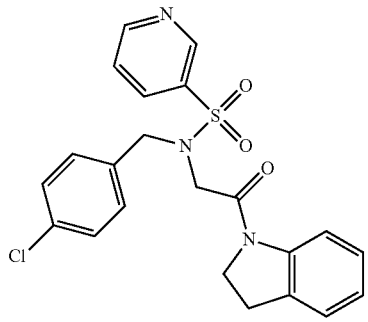 [SMILES: O=C(CN(Cc1ccc(Cl)cc1)S(=O)(=O)c1cccnc1)N1CCc2ccccc21]

and pharmaceutically acceptable salts thereof.

18. The method according to claim 17, wherein the compound is selected from the following table:

5 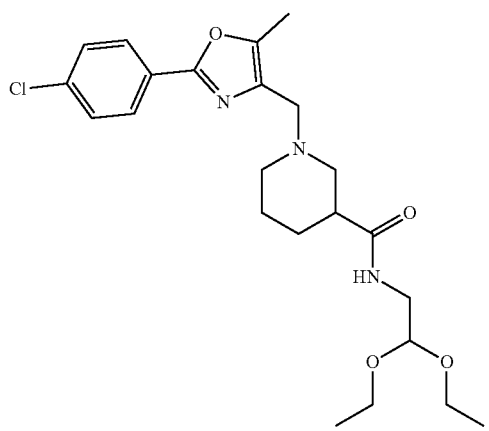

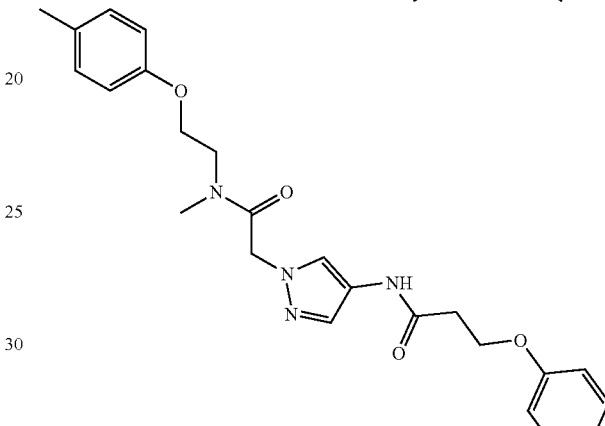

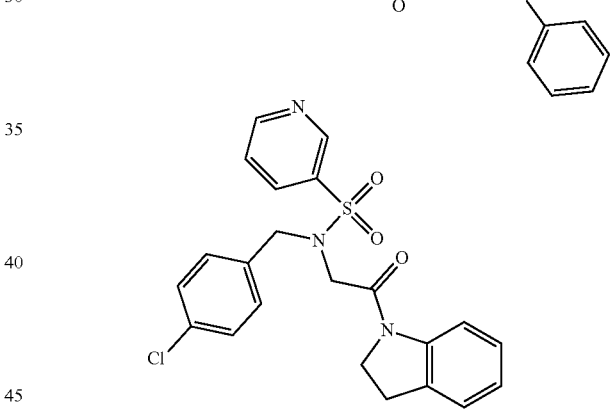

and pharmaceutically acceptable salts thereof.

19. The method according to claim 12, wherein the disease or condition is a neurodegenerative disease selected from the group consisting of Parkinson's disease, Huntington's disease, and peripheral nerve injury.

20. The method of claim 11, wherein the compound activates the inositol-requiring enzyme 1 (IRE1)/X-box binding protein 1 (XBP1s) signaling pathway of the unfolded protein response (UPR) at a level 1.5-2.0 times higher than ATF6 transcriptional signaling.

21. A method for selectively activating the inositol-requiring enzyme 1 (IRE1)/X-box binding protein 1 (XBP1s) signaling pathway of the unfolded protein response (UPR) independent of other UPR signaling pathways, comprising administering to a cell a compound or a pharmaceutically acceptable salt thereof wherein the compound does not inhibit IRE1 kinase activity.

22. The method of claim 21, wherein the compound activates the inositol-requiring enzyme 1 (IRE1)/X-box binding protein 1 (XBP1s) signaling pathway of the unfolded protein response (UPR) at a level 1.5-2.0 times higher than ATF6 transcriptional signaling.

* * * * *